United States Patent
Wiencierz et al.

(10) Patent No.: US 9,717,762 B2
(45) Date of Patent: Aug. 1, 2017

(54) COMPOSITIONS OF CARDIOMYOCYTE SUBPOPULATIONS

(71) Applicant: Miltenyi Biotec GmbH, Bergisch Gladbach (DE)

(72) Inventors: Anne Maria Wiencierz, Cologne (DE); Dominik Eckardt, Bergisch Gladback (DE); Andreas Bosio, Cologne (DE)

(73) Assignee: Miltenyi Biotec, Bergisch Gladbach (DE)

(*) Notice: Subject to any disclaimer, the term of this patent is extended or adjusted under 35 U.S.C. 154(b) by 0 days.

(21) Appl. No.: 14/547,994

(22) Filed: Nov. 19, 2014

(65) Prior Publication Data

US 2015/0160237 A1   Jun. 11, 2015

(30) Foreign Application Priority Data

Nov. 20, 2013   (EP) .................................. 13193641

(51) Int. Cl.
*A61K 35/34* (2015.01)
*C12N 5/00* (2006.01)
*G01N 33/569* (2006.01)
*C12N 5/077* (2010.01)

(52) U.S. Cl.
CPC ............... *A61K 35/34* (2013.01); *C12N 5/00* (2013.01); *C12N 5/0657* (2013.01); *G01N 33/56966* (2013.01); *G01N 2333/7055* (2013.01)

(58) Field of Classification Search
CPC .... A61K 35/34; C12N 5/00; G01N 33/56966; G01N 2333/7055
See application file for complete search history.

(56) References Cited

U.S. PATENT DOCUMENTS

2008/0070830 A1* 3/2008 Dzau ...................... A61K 31/70
424/93.21

FOREIGN PATENT DOCUMENTS

| WO | WO 2008/058273 A2 | 5/2008 |
| WO | WO 2011/005930 A1 | 1/2011 |
| WO | WO 2011/157029 A1 | 12/2011 |

OTHER PUBLICATIONS

Hierck et al. (Differential Expression of Alpha 6 and Other Subunits of Laminin Binding Integrins During Development of the Murine Heart. Developmental Dynamics 206: 100-111 (1996).*
Pentassuglia et al. The Role of Neuregulin 1 Beta/ErbB signaling in the heart. Exp Cell Res. (Feb. 15, 2009)).*
Oh et al. Cardiac progenitor cells from adult myocardium: Homing, differentiation, and fusion after infarction. PNAS 100 (21): 12313-12318 (Oct. 14, 2003)).*
"Data Sheet 4—CD49e antibodies, mouse", MACS, Miltenyi Biotec, 2011, downloaded from www.miltenyi.biotec on Mar. 9, 2015, Version 02, revised Jan. 10, 2015, 3 pages.
(Continued)

*Primary Examiner* — Gail R Gabel
(74) *Attorney, Agent, or Firm* — Kilpatrick Townsend and Stockton LLP

(57) ABSTRACT

The present invention provides the use of the antigens CD49e and/or CD49f as selection markers for enrichment, isolation, detection and/or analysis of atrial and ventricular cardiomyocytes and a method for enrichment, isolation, detection and/or analysis of these cells from a sample comprising cardiomyocytes. In addition substantially pure compositions of these cardiomyocyte subpopulations are provided.

22 Claims, 18 Drawing Sheets

(56) References Cited

OTHER PUBLICATIONS

"Data Sheet 4—CD49f antibodies, human and mouse", MACS, Miltenyi Biotec, 2012, downloaded from www.miltenyi.biotec on Mar. 9, 2015, 2 pages.

"Data Sheet 4—CD61 antibodies, human", MACS, Miltenyi Biotec, 2013, downloaded from www.miltenyi.biotec on Mar. 9, 2015, 2 pages.

Ban et al., "Purification of Cardiomyocytes from Differentiating Pluripotent Stem Cells Using Molecular Beacons that Target Cardiomyocyte-Specific mRNA", Circulation, Aug. 2013, vol. 128, p. 1897-1909.

Bizy et al., "Myosin light chain 2-based selection of human iPSC-derived early ventricular cardiac myocytes", Stem Cell Research, 2013, vol. 11, Issue 3, p. 1335-1347.

Chuva de Sousa Lopes et al., "Patterning the Heart, a Template for Human Cardiomyocyte Development", Developmental Dynamics, Jul. 2006, vol. 235, Issue 7, p. 1994-2002.

Hattori et al., "Nongenetic method for purifying stem cell-derived cardiomyocytes", Nature Methods, Jan. 2010, vol. 7 No. 1, pp. 61-66.

Hermann et al., "Adaptive Recognition by Nucleic Acid Aptamers", Science, vol. 287, Feb. 4, 2000, p. 820-825.

Hescheler et al., "Embryonic stem cells: a model to study structural and functional properties in cardiomyogenesis", Cardiovascular Research, 1997, vol. 36, p. 149-162.

Hierck et al., "Differential expression of alpha-6 and other subunits of laminin binding integrins during development of the murine heart", Developmental Dynamics, May 1996, 206:100-111.

Hirata et al., "ALCAM (CD166) Is a Surface Marker for Early Murine Cardiomyocytes", Cells Tissues Organs, 2006, vol. 184, No. 3-4, p. 172-180.

Leri et al., "Telomerase expression and activity are coupled with myocyte proliferation and preservation of telomeric length in the failing heart", PNAS, Jul. 17, 2001, vol. 98, No. 15, p. 8626-8631.

Maitra et al., "Expression of alpha and beta integrins during terminal differentiation of cardiomyocytes", Cardiovascular Research, Sep. 2000, vol. 4, Issue 4, p. 715-725.

Oh et al., "Cardiac progenitor cells from adult myocardium: Homing, differentiation, and fusion after infarction", PNAS, Oct. 14, 2003, vol. 100, No. 21, p. 12313-12318.

Oh et al., "Telomerase reverse transcriptase promotes cardiac muscle cell proliferation, hypertrophy, and survival", PNAS, Aug. 28, 2001, vol. 98, No. 18, p. 10308-10313.

Pentassuglia et al., "The role of Neuregulin-1β/ErbB signaling in the heart", Experimental Cell Research, Feb. 2009, vol. 315, Issue 4, p. 627-637.

Ponten et al., "FACS-based isolation, propagation and characterization of mouse embryonic cardiomyocytes based on VCAM-1 surface marker expression", PLoS One, Dec. 2013, vol. 8, Issue 12, e82403.

Ross et al., "Integrins and the Myocardium", Circulation Research, Jun. 2001, vol. 88, Issue 11, p. 1112-1119.

Rust et al., "Cardiomyocyte enrichment from human embryonic stem cell cultures by selection of ALCAM surface expression", Regen Med, Mar. 2009, vol. 4, Issue 2, p. 225-237.

Shamblott et al., "Human embryonic germ cell derivatives express a broad range of developmentally distinct markers and proliferate extensively in vitro", PNAS, Jan. 2, 2001, vol. 98, No. 1, p. 113-118.

Tohyama et al., "Distinct Metabolic Flow Enables Large-Scale Purification of Mouse and Human Pluripotent Stem Cell-Derived Cardiomyocytes", Cell Stem Cell, Jan. 2013, vol. 12, Issue 1, p. 127-137.

Uosaki et al., "Efficient and Scalable Purification of Cardiomyocytes from Human Embryonic and Induced Pluripotent Stem Cells by VCAM1 Surface Expression", PLoS One, Aug. 2011, 6:e23657.

Urbanek et al., "Intense myocyte formation from cariac stem cells in human cardiac hypertrophy", PNAS, Sep. 2, 2003, vol. 100, No. 18, p. 10440-10445.

Urbanek et al., "Myocardial regeneration by activation of multipotent cardiac stem cells in ischemic heart failure", PNAS, Jun. 14, 2005, vol. 102, No. 24, p. 8692-8697.

Walsh, "Cardiomyocyte Cell Cycle, Renewal and Isolation", Lund University, Faculty of Medicine Doctoral Dissertation Series 2010:44, 2010, 58 pages.

Wu et al., "Cellular therapy and myocardial tissue engineering: the role of adult stem and progenitor cells", European Journal of Cardio-Thoracic Surgery, 30, (2006), p. 770-781.

International Search Report and Written opinion for PCT/US2010/041327, mailed on Oct. 18, 2010, 5 pages.

European Application No. 13193641.1, Examination Report from European Patent Office in corresponding application in Europe, dated Dec. 23, 2016, 5 pages.

Brancaccio et al., "Differential Onset of Expression of α7 and β1D Integrins During Mouse Heart and Skeletal Muscle Development", Cell Adhesion and Communication, 1998, vol. 5, pp. 193-205.

\* cited by examiner

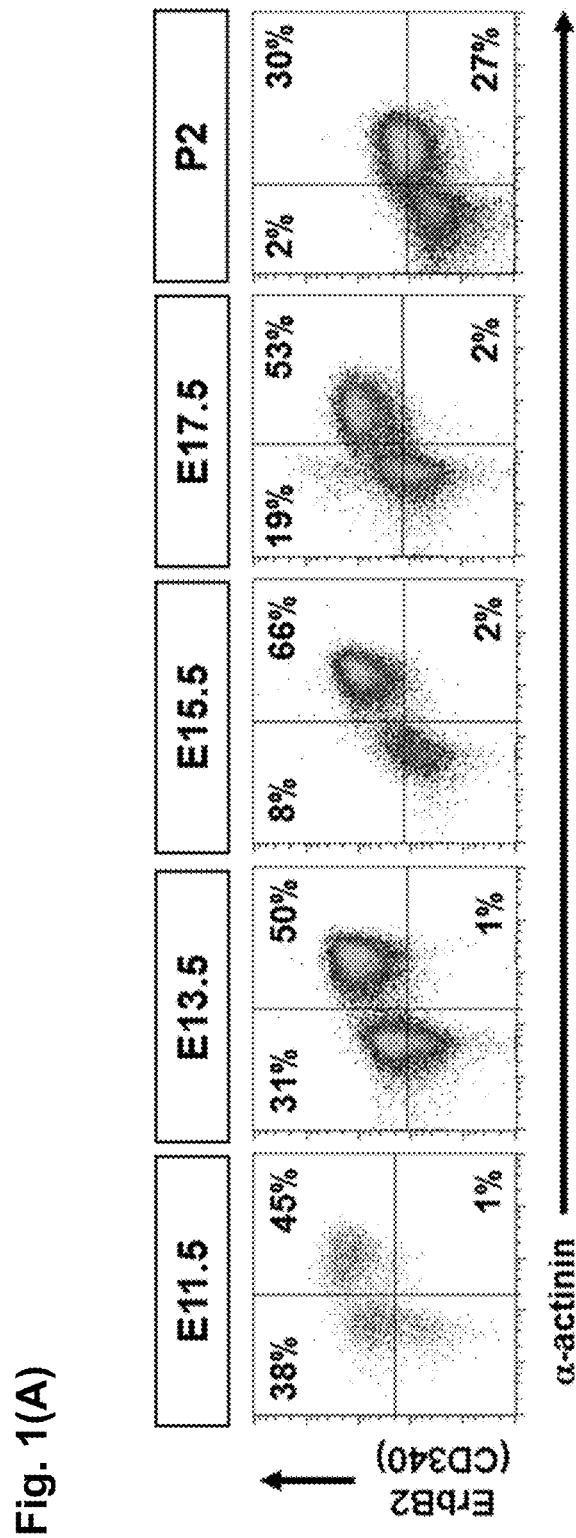

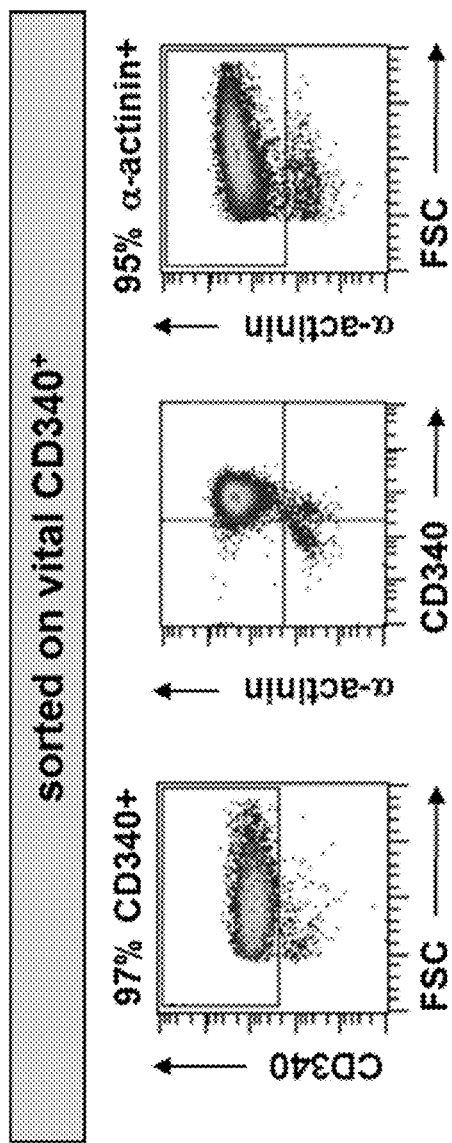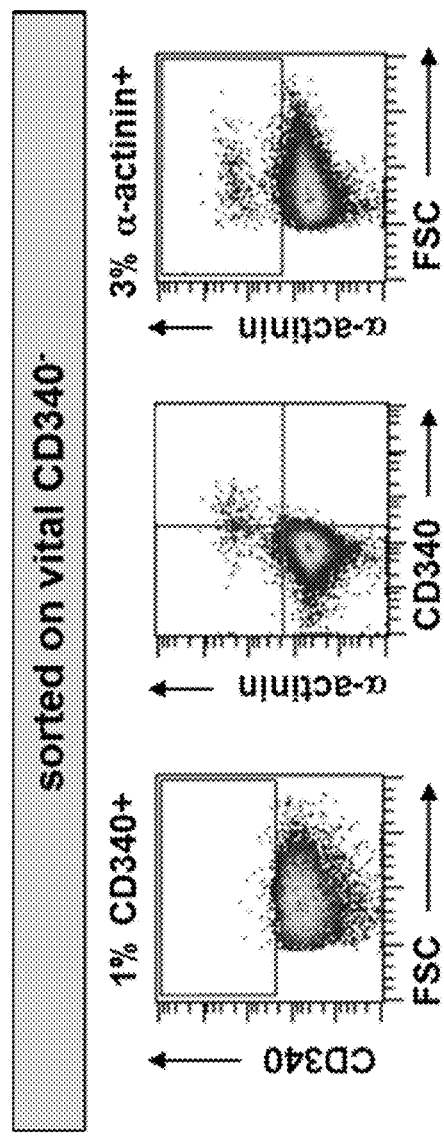

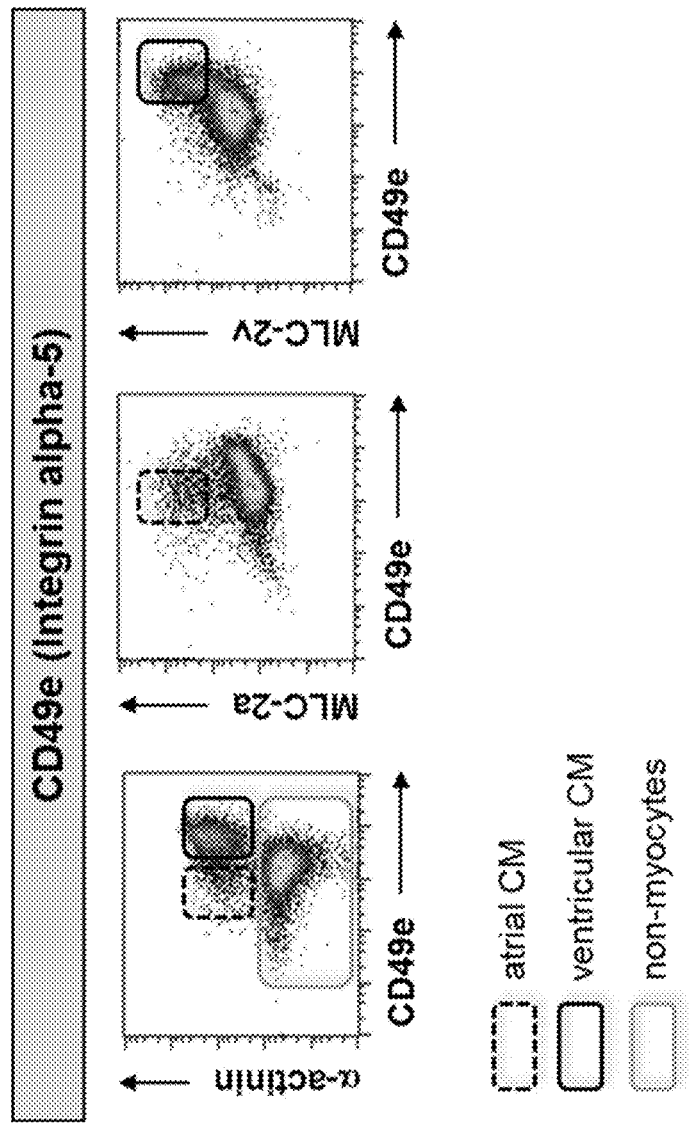

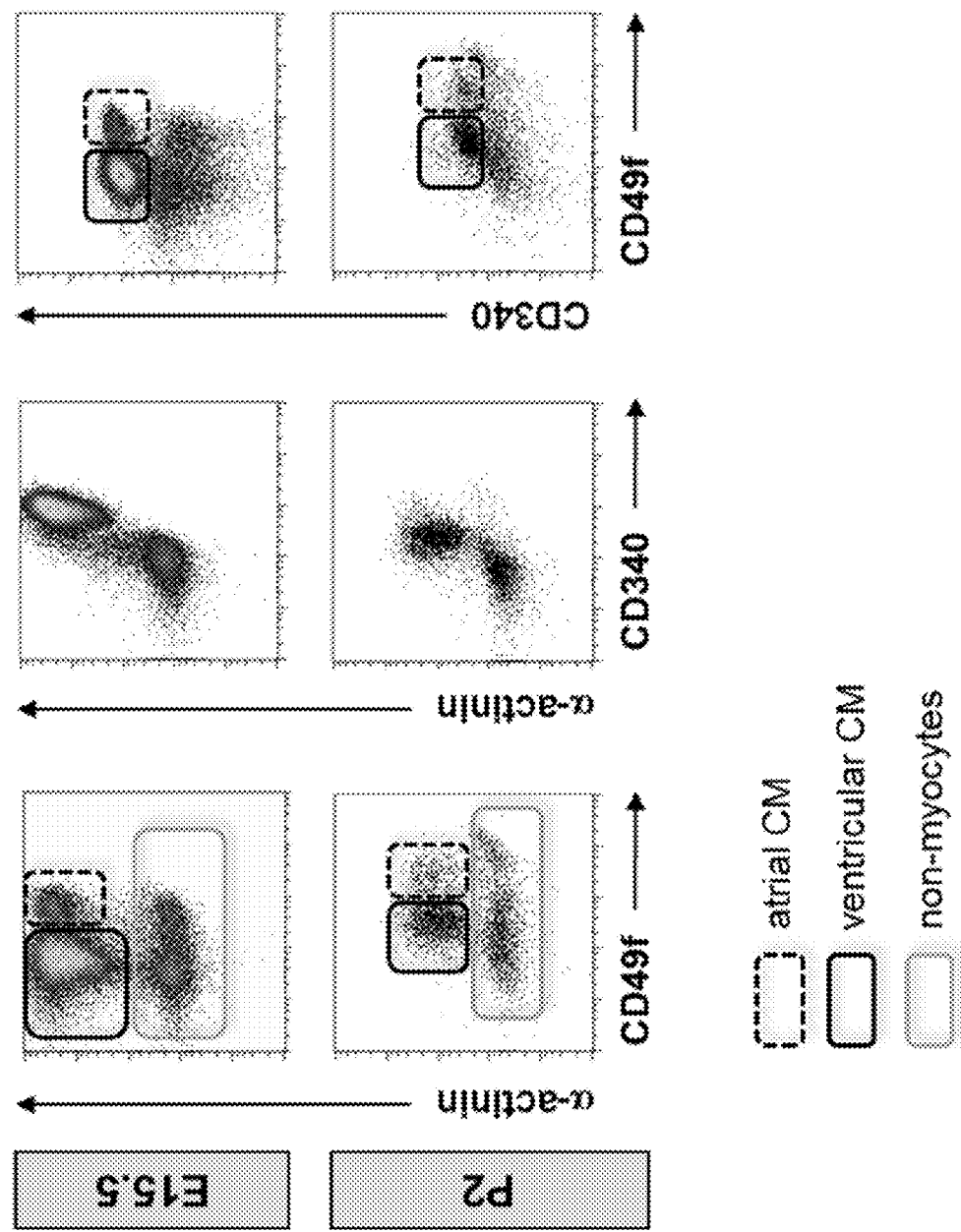

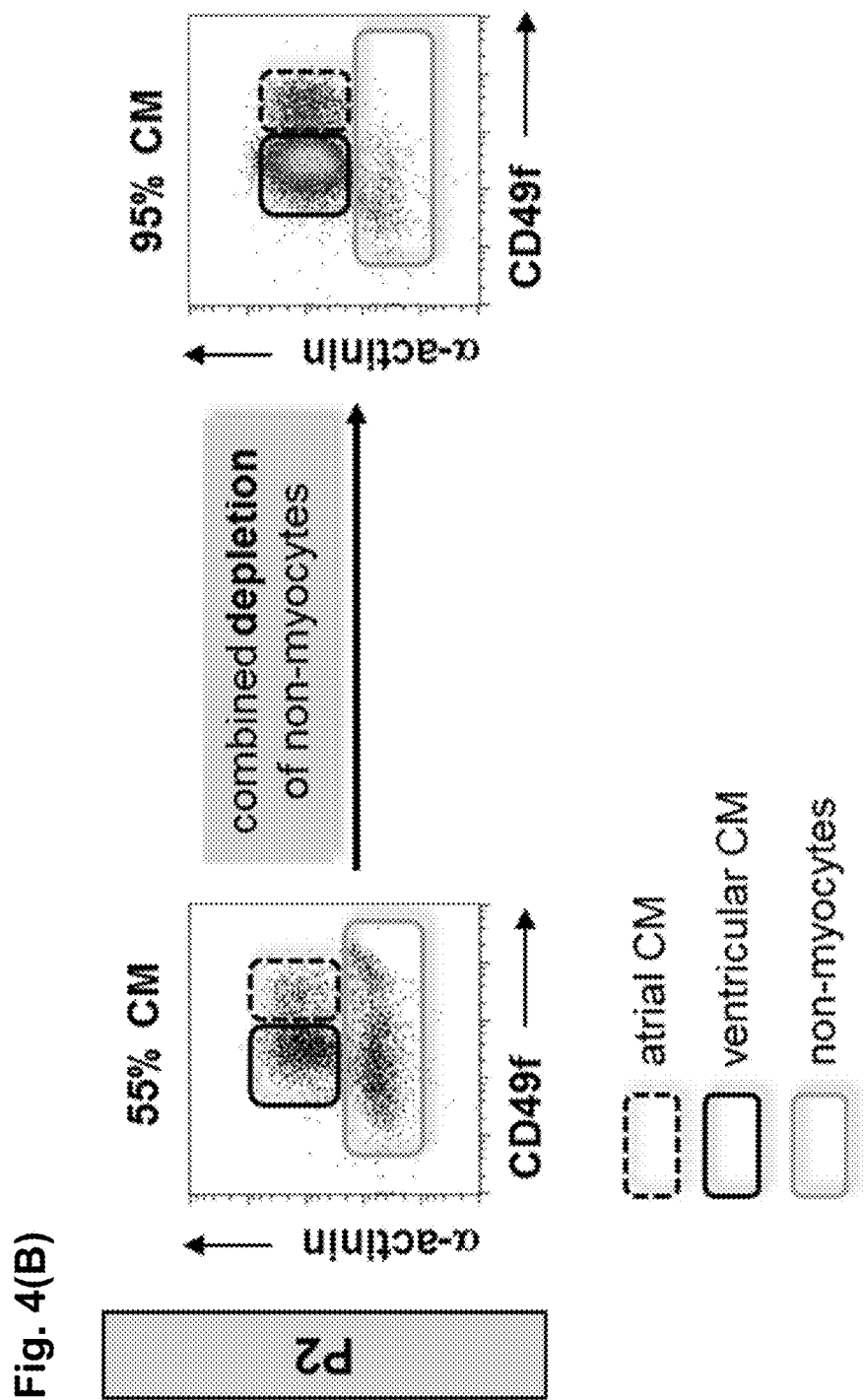

Fig. 4(H)

| Gene | Name | E15.5 | P2 |
|---|---|---|---|
| Gm1078 | predicted gene 1078 | 47,4 | 136,6 |
| Camk1d | calcium/calmodulin-dependent protein kinase ID | 35,4 | 135,8 |
| Mrvi1 | murine retrovirus integration site 1 homolog | 13,4 | 135,3 |
| Mybphl | myosin binding protein H-like | 81,6 | 125,5 |
| Fgf12 | fibroblast growth factor 12 | 119,2 | 122,9 |
| Npy1r | neuropeptide Y receptor Y1 | 27,4 | 100,8 |
| Nr2f1 | COUP-TFI; nuclear receptor subfamily 2, group F, member 1 | 65,4 | 100,2 |
| Mlana | melan-A | 7,7 | 94,5 |
| Nr2f2 | COUP-TFII; nuclear receptor subfamily 2, group F, member 2 | 23,7 | 76,6 |
| Sln | Sarcolipin | 74,3 | 72,3 |
| Dkk3 | dickkopf 3 homolog (Xenopus laevis) | 15,1 | 72,3 |
| Uts2d | urotensin 2 domain containing | 77,3 | 61,2 |
| Myl7 | MLC-2a; myosin, light chain 7, regulatory | 15,0 | 60,5 |
| Slc24a4 | Na(+)/K(+)/Ca(2+)-Exchange Protein 4 | 11,0 | 54,5 |
| Bmp10 | bone morphogenetic protein 10 | 29,5 | 51,0 |
| Gja5 | Connexin 40; gap junction protein, alpha 5, 40kDa | 9,7 | 42,4 |
| Myl1 | myosin, light chain 1, alkali; skeletal, fast | 75,5 | 38,0 |
| Kcnj3 | Kir3.1; potassium inwardly-rectifying channel, subfamily J, member 3 | 18,0 | 32,5 |
| Itga6 | CD49f; integrin, alpha 6 | 19,1 | 22,8 |
| Gpx3 | glutathione peroxidase 3 (plasma) | 6,6 | 21,9 |
| Nppa | ANF; natriuretic peptide A | 20,3 | 19,5 |
| Tbx5 | T-box 5 | 6,6 | 11,6 |
| Ap3b2 | adaptor-related protein complex 3, beta 2 subunit | 124,2 | 8,6 |
| Hey1 | HRT-1; hairy/enhancer-of-split related with YRPW motif 1 | 6,2 | 7,1 |

Fig. 4(I)

| Gene | Name | E15.5 | P2 |
|---|---|---|---|
| Hey2 | HRT-2; hairy/enhancer-of-split related with YRPW motif 2 | -30,8 | -67,1 |
| Irx4 | iroquois homeobox 4 | -5,0 | -47,5 |
| Smyd2 | SET and MYND domain containing 2 | -3,1 | -46,4 |
| Prdm16 | PR domain containing 16 | -10,8 | -40,2 |
| Ush1c | Usher syndrome 1C | -13,9 | -37,0 |
| Adamtsl5 | ADAMTS-like 5 | -4,0 | -33,3 |
| Nkd2 | naked cuticle homolog 2 (Drosophila) | -15,7 | -32,0 |
| Tox | thymocyte selection-associated high mobility group box | -6,1 | -25,9 |
| Alox5 | arachidonate 5-lipoxygenase | -6,8 | -24,4 |
| Myh7 | myosin, heavy chain 7, cardiac muscle, beta | -3,1 | -22,3 |
| Upp1 | uridine phosphorylase 1 | -11,0 | -21,9 |
| Prr9 | proline rich 9 | -4,7 | -21,2 |
| Ntn4 | Netrin-4 | -3,6 | -20,6 |
| Wdr72 | WD repeat domain 72 | -14,8 | -20,2 |
| Slc35f1 | solute carrier family 35, member F1 | -10,7 | -18,6 |
| Grik3 | glutamate receptor, ionotropic, kainate 3 | -30,9 | -16,2 |
| Sun3 | Sad1 and UNC84 domain containing 3 | -7,5 | -12,7 |
| Kcnj4 | Kir2.3; potassium inwardly-rectifying channel, subfamily J, member 4 | -4,8 | -11,3 |
| Cachd1 | cache domain containing 1 | -5,0 | -11,1 |
| Cx3cl1 | chemokine (C-X3-C motif) ligand 1 | -5,8 | -9,6 |
| Gipc2 | GIPC PDZ domain containing family, member 2 | -5,8 | -7,8 |
| Lbh | limb bud and heart development | -5,7 | -7,2 |
| Dio2 | deiodinase, iodothyronine, type II | -8,1 | -3,9 |
| Rnf182 | ring finger protein 182 | -8,2 | -3,5 |

COMPOSITIONS OF CARDIOMYOCYTE SUBPOPULATIONS

CROSS-REFERENCE TO RELATED APPLICATION

This application claims the priority benefit of European application EP 13193641, filed Nov. 20, 2013, entitled "Compositions of Cardiomyocyte Subpopulations". The contents of the priority application are hereby incorporated herein by reference in their entirety for all purposes.

FIELD OF THE INVENTION

The present invention relates generally to the field of cardiomyocytes, in particular to atrial and ventricular cardiomyocytes, to methods for separation, detection, enrichment, isolation and to uses of these cells.

BACKGROUND OF THE INVENTION

Hearts are made up of different cell populations, such as cardiomyocytes, fibroblasts, endothelial and smooth muscle cells. Atrial and ventricular cardiomyocytes are of special interest in heart research and regenerative medicine. They are naturally located within the mammalian heart and can as well be derived from other cell types, e.g. stem cells, by inductive cues. Several intracellular proteins like muscle proteins and/or transcription factors have been described as being differentially expressed in atrial or ventricular cardiomyocytes; atrial cardiomyocytes are characterized e.g. by gene expression of Myl7, Fgf12, Sln, Gja5, Nppa, Tbx5, ventricular cardiomyocytes are characterized e.g. by gene expression of Hey2, Irx4, Lbh, Myh7.

In mouse development, the four-chambered heart is formed by embryonic day (E) 10.5. The sequence of morphological events coincides with chamber-restricted expression of individual sarcomeric proteins in cardiomyocytes of atria and ventricles. As described by Chuva de Sousa Lopes S M et al. ((2006) Dev Dyn 235(7):1994-2002), mRNA of the atrial intracellular muscle protein, myosin light chain 2a (MLC-2a), is highly expressed in the atria, weakly expressed in the trabeculated and undetectable in the compacted myocardium of the ventricles from E14.5 on. Opposite expression is described for the mRNA of the ventricular intracellular muscle protein (MLC-2v), which was found to be expressed in both ventricles but absent in the atria. After birth, expression of both markers is even more restricted to either atria or ventricles. To date, expression of intracellular proteins enriched either in atrial or ventricular cardiomyocytes could not be correlated to corresponding cell surface markers enabling selective cell enrichment of either atrial or ventricular cardiomyocytes. Therefore, it is currently impossible to purify atrial and ventricular cardiomyocytes from mixed cell populations as well as from mixed cardiomyocyte populations by means of cell surface marker-based cell separation procedures.

The expression patterns of key cardiac genes during in vitro pluripotent stem cell (PSC) differentiation is known to closely reflect their endogenous expression during in vivo cardiogenesis and PSC-derived cardiomyocytes share functional characteristics with embryonic cardiomyocytes (Hescheler et al. (1997) Cardiovasc Res 36:149-162). A major issue is still the heterogeneity of cell populations generated by in vitro differentiation protocols. Besides contaminating non-cardiomyocytes, most differentiation protocols generate a mixture of cardiomyocyte subpopulations, like atrial, ventricular and pacemaker cardiomyocytes. Although differentiation protocols favouring generation of cardiomyocyte subpopulations have been reported, neither generation of pure cardiomyocyte subpopulations nor surface marker-based enrichment of individual subpopulations have been described. Cardiomyocytes are usually identified by antibody-based immunofluorescence analysis, using antibodies against cardiomyocyte-specific transcription factors or sarcomeric proteins or electrophysiological measurements. All known subtype-specific proteins are intracellularly localized and thus prevent isolation of viable cells, because the antibodies are not able to bind intracellular components without destroying cells by permeabilization to allow for antibody penetrance, thereby limiting downstream analysis and preventing use of viable cardiomyocyte subpopulations.

Although general cell surface markers of primary and PSC-derived cardiomyocytes, unable to discriminate between atrial and ventricular cardiomyocytes, have been described and surface marker-based enrichment has been performed e.g. with human PSC-derived cardiomyocytes, methods for separation of primary or PSC-derived cardiomyocytes into subpopulations of atrial and ventricular cardiomyocytes by means of surface marker-based cell purification methods are still missing.

Cell surface marker-independent experimental procedures have been described to enrich cardiomyocytes from mixed cell populations, but are still unable to discriminate between atrial and ventricular cardiomyocytes: 1) physical separation based on size: cardiomyocytes accumulate in a specific layer of a Percoll® gradient. This method is laborious, gives purities of 75-90% as well as very weak cell yield. 2) fluorescent reporter or antibiotic resistance genes that are driven by a cardiomyocyte- or subtype-specific promoters, e.g. myosin light chain (Bizy et al. (2013) Stem Cell Res 11:1335-1347). This yields >90% cardiomyocytes after FACSorting or antibiotic selection, but requires genetic modification of every single cell or mouse line and is neither broadly applicable nor useful for clinical translation. 3) Molecular beacons that emit a fluorescence signal when hybridized to target mRNAs, like cardiac troponin T or myosin light chains (Ban et al. (2013) Circulation 128:1897-1909). This method again requires (genetic) modification of cells by transfection of respective molecular beacons. 4) High abundance of cellular mitochondria is a common characteristic of primary cardiomyocytes. Therefore, intracellular labeling of cardiomyocytes with mitochondrial dyes like MitoTracker® Red has been described as a tool to enrich cardiomyocytes by FACSorting (Hattori et al. (2010) Nat Methods 7:61-66), but turned out to be useful only in primary cardiomyocytes that accumulated high numbers of mitochondria. 5) Metabolic selection of cultured cardiomyocytes by exchange of glucose with lactate in the culture medium has been described as a means to enrich for cardiomyocytes (Tohyama et al. (2013) Cell Stem Cell 12:127-137); major disadvantages of this method are a lengthy selection period (several days) as well as weak recoveries of cardiomyocytes.

None of these methods can be used to selectively enrich for cardiomyocyte subpopulations, i.e. atrial and ventricular cardiomyocytes from mixed cell populations. Besides, several cell surface markers have been identified on primary or PSC-derived cardiomyocytes, but not on atrial or ventricular cardiomyocyte subpopulations and hence are not suitable for the discrimination of atrial and ventricular cardiomyocytes. Most cell surface markers described so far are expressed on cardiomyocytes as well as on non-cardiomyocytes, like CD106 (VCAM-1), CD166 (ALCAM), CD340 (ErbB2) and CD61 (Integrin beta-3).

Stuart Walsh ((2010) Dissertation, Lund University; ISBN 978-91-86443-59-7) identified VCAM-1 (CD106) as cardiomyocyte cell surface marker by flow cytometry analysis of alpha-MHC promoter-eGFP expression in embryonic mouse heart cells. FACS sorting revealed that >97% of CD106$^+$/CD31$^-$ sorted cells from embryonic day 10.5-11.5 embryos were also positive for the cardiac muscle protein Troponin T. Sorted cells expressed cardiac specific structural proteins including alpha-MHC, MLC-2a and MLC-2v, indicating that this cell surface marker labels atrial and ventricular cardiomyocytes and does not allow for subtype-specific isolation. Antibodies against VCAM-1 could as well be used to purify a mixture of ventricular-like and pacemaker-like cardiomyocytes derived from human PSCs. (Uosaki et al. (2011) PLoS One 6:e23657). Hirata et al. ((2006) Cells Tissues Organs 184:172-80) identified ALCAM (CD166) as general surface marker for cardiomyocytes in mouse hearts between embryonic day 8.25 and 10.5 by immunofluorescence analysis. Additionally, Rust et al. ((2009) Regen Med 4:225-237) used antibody-based enrichment of ALCAM-positive, human PSC-derived cardiomyocytes. Nevertheless, ALCAM expression cannot be used to discriminate between cardiomyocyte subpopulations.

Although not yet explicitly described for antibody-based cardiomyocyte enrichment, expression of CD340 (ErbB2) and ErbB4 in primary and human/mouse PSC-derived cardiomyocytes of the working myocardium is known (e.g. Pentassuglia and Sawyer (2009) Exp Cell Res 315:627-637). Expression of several integrin family members in cardiomyocytes is described: alpha-1, alpha-3, alpha-5 (CD49e), alpha-6 (CD49f), alpha-7, alpha-9, and alpha-10 as well as beta subunits beta-1, beta-3 (CD61) and beta-5 were found to be expressed in primary or PSC-derived cardiomyocytes. The main integrin heterodimers on the cardiomyocyte surface are alpha-5/beta-1 and alpha v/beta-3 (Ross and Borg (2001) Circ Res 88:1112-1119). Characterization of integrin family member distribution based on in situ hybridization (mRNA) and immunohistochemistry (protein) analysis found high expression of integrin alpha-6 (CD49f) in the atria throughout development. Integrin alpha-6 is absent from the compact layer of the ventricles, but highly expressed in the ventricular trabeculae from E15 onwards. Additionally, integrin alpha-6 expression in the endocardium reaches a peak at E18, including all coronary endothelial cells. Extracardially, alpha-6 was found in endothelium, epithelia, and nervous tissue (Hierck et al. (1996) Dev Dyn 206:100-111). These data clearly indicate a simultaneous expression of integrin alpha-6 in atrial and ventricular cardiomyocytes as well as non-cardiomyocytes during heart development. Single cell analysis as well as a direct correlation of integrin alpha-6 expression with cardiomyocyte subpopulation specific, intracellular proteins expression (e.g. MLC-2a) in the same cell is missing. Additionally, no data are provided on technology development using integrin expression patterns for the development of cell separation strategies for selective enrichment of atrial and/or ventricular cardiomyocytes.

The current inability to enrich for atrial and/or ventricular cardiomyocytes from mixed cell populations containing cardiomyocytes and non-cardiomyocytes or preparations of cardiomyocytes containing mixtures of cardiomyocyte subpopulations by a surface marker-based enrichment method, prevents the use of atrial and/or ventricular cardiomyocytes for downstream applications like:

a) individual drug screening approaches on enriched atrial or ventricular cardiomyocytes
b) cell replacement therapy using enriched cardiomyocyte subpopulations, e.g. ventricular-like cardiomyocytes for transplantation into the ventricle, atrial-like cardiomyocytes for transplantation into the atrium
c) characterization of cardiomyocyte subtype emergence during heart development
d) selective targeting of cardiomyocyte subpopulations for gene therapy and drug delivery applications, using e.g. cardiomyocyte subtype-specific single chain antibodies Therefore, there is a need in the art for a method for enrichment, isolation, detection and/or analysis of atrial and ventricular cardiomyocytes.

SUMMARY OF THE INVENTION

The present invention provides the use of cell surface markers for enrichment, isolation, detection and/or analysis of cardiomyocyte subpopulations. A cell surface marker-based method for enrichment, isolation, detection and/or analysis of cardiomyocyte subpopulations is a gentle method for enrichment, isolation, detection and/or analysis of e.g. viable and unmodified cardiomyocyte subpopulations. These cell surface markers were found to be specific for atrial and ventricular cardiomyocytes. The present invention further provides compositions of cardiomyocyte subpopulations as well as uses thereof.

We surprisingly found that:
1) CD49e (integrin alpha-5), is a surface marker for atrial and ventricular cardiomyocytes and allows for corresponding enrichment of primary and PSC-derived cardiomyocyte subpopulations.
2) CD49f (integrin alpha-6) is a surface marker for atrial and ventricular cardiomyocytes and allows for corresponding enrichment of primary and PSC-derived cardiomyocyte subpopulations.
3) CD61 (integrin beta-3) is a surface marker for stem cell-derived murine cardiomyocytes and allows for enrichment of murine PSC-derived cardiomyocytes.
4) CD112 (Nectin-2), CD146 (MCAM) and CD340 (ErbB2) are general surface markers for cardiomyocytes and allow for enrichment of primary and PSC-derived cardiomyocyte subpopulations.
5) Combinatorial labeling of cardiomyocytes with an antibody against a general cardiomyocyte surface marker, e.g. CD340, plus an antibody against CD49e or CD49f allows for subtype-specific detection and enrichment with high purities.
6) An antibody-based screen of non-cardiomyocytes in primary heart cell suspensions and PSC-derived cell suspensions revealed following surface markers of non-cardiomyocytes: Sca-1, CD15, CD31, CD38, CD45, CD49b, CD49d, CD54, CD66a, CD73, CD90.1, CD90.2, CD105, CD117, CD138, CD140a, CD140b, CD184, CD326. Non-cardiomyocytes within mixed cell populations comprising cardiomyocytes and non-cardiomyocytes can be removed by antibody-based depletion of non-cardiomyocytes targeting aforementioned surface markers of non-cardiomyocytes. Thereby, "untouched" cardiomyocytes, i.e. cardiomyocytes not labeled with antibodies are enriched. From this population of "untouched" cardiomyocytes, cardiomyocyte subpopulations can be isolated selectively using antibodies/ligands against/for the subtype-specific surface markers, i.e. CD49e and CD49f.

We identified these cell surface markers that enable for e.g. antibody/ligand-based, specific enrichment, isolation, detection and/or analysis of cardiomyocyte subpopulations and/or cardiomyocytes from mixed cell populations as well as surface markers, specifically expressed on non-cardiomyocytes, enabling for "untouched" enrichment of cardiomyocytes. Use of surface marker-based enrichment of cardiomyocyte subpopulations will for the first time allow for individual characterization and use of e.g. viable and/or unmodified cardiomyocyte subpopulations e.g. in cardiac and translation research as well as cell therapeutic applications.

BRIEF DESCRIPTION OF THE FIGURES

FIGS. 1(A) and 1(B) show identification and isolation of murine cardiomyocytes by CD340. In FIG. 1(A), flow cytometry analysis showed that CD340 was expressed by murine cardiomyocytes at different embryonic stages (E11.5, E13.5, E15.5, E17.5), but was down-regulated after birth (P2). In FIG. 1(B), flow cytometry analysis showed that cardiomyocytes taken from the E15.5 stage contained both CD340 negative and CD340 positive cells. In FIG. 1(C), fluorescence-activated cell sorting (FACS) of CD340+ cells from embryonic mouse hearts (E15.5) resulted in an efficient purification of cardiomyocytes (95% alpha-actinin+) in the CD340+ fraction. In FIG. 1(D), only 3% of the CD340-population were alpha-actinin+.

In FIG. 2(A), antibody-based surface marker screening of embryonic mouse hearts (E13.5), mechanically separated into atrial and ventricular fraction, identified CD112, CD146, CD49e and CD49f as novel cardiomyocyte surface markers. Surprisingly, antibody labeling of CD49e and CD49f displayed subpopulation-specific fluorescence intensities with a stronger fluorescence signal in ventricular cardiomyocytes for CD49e (CD49e$^{high}$) and a stronger CD49f (CD49f$^{high}$) signal in atrial cardiomyocytes. In FIG. 2(B), co-labeling of embryonic mouse hearts (E13.5) with antibodies against CD49e or CD49f and antibodies against atrium- or ventricle-specific muscle proteins, clearly demonstrates that CD49f$^{high}$ and CD49f$^{low}$ subpopulations correspond to MLC-2a and MLC-2v expression, respectively. In FIG. 2(C), the CD49e$^{high}$ subpopulation corresponds to MLC-2v+ while the CD49e$^{low}$ subpopulation corresponds to MLC-2a+.

FIGS. 4(A) and 4(B) show enrichment of cardiomyocyte subpopulations. FIG. 4(A) shows Isolation Strategy "1", in which a combination of antibodies against the surface markers CD340 and CD49f was used to specifically identify atrial and ventricular cardiomyocytes (E15.5, P2). FIG. 4(B) shows Isolation Strategy "2", in which pre-enrichment of cardiomyocytes by antibody-based depletion of non-cardiomyocytes was followed by antibody-based labeling of the surface marker CD49f to specifically identify atrial and ventricular cardiomyocytes (P2). FIG. 4(C) shows marker distribution before separation using CD49f. After separation, cytometric re-analysis of the isolated subpopulations revealed efficient purification of cardiomyocytes (>95%) in both the CD49f$^{high}$ and CD49f$^{low}$ subpopulations (FIGS. 4(D) and 4(E)). Furthermore, the CD49f$^{high}$ subpopulation was specifically enriched for MLC-2a+ cells (from 9% up to 70%) whereas the CD49f$^{low}$ subpopulation was enriched for MLC-2v+ cells (94%). FIGS. 4(H) and 4(I) show the results of microarray analysis of CD49f$^{high}$ and CD49f$^{low}$ sorted murine hearts (E15.5, P2). In FIG. 4(H), atrial marker genes were up-regulated in the CD49f$^{high}$ subpopulation. In FIG. 4(I), ventricle-specific marker genes were up-regulated in the CD49f$^{low}$ subpopulation.

FIG. 5(F) is a FACS analysis of the surface markers expressed on mESC-derived cardiomyocytes before sorting.

After separation for the markers CD340 and CD49f according to Isolation Strategy "1", the subpopulations of CD49f$^{high}$ and CD49f$^{low}$ cells were re-analyzed for marker expression (FIGS. 5(G) and 5(H)). FIG. 5(I) shows Isolation Strategy "2" as applied to mESC derived cardiomyocytes. The cells were processed by antibody-based depletion of non-cardiomyocytes followed by labeling of the surface marker CD49f.

FIGS. 5(J), 5(K), 5(L) and 5(M) show marker analysis of cardiomyocytes derived from human pluripotent stem cells. These cells were MLC-2a+ and co-expressed CD49f, CD49e and CD340.

DETAILED DESCRIPTION OF THE INVENTION

Figure 1B:
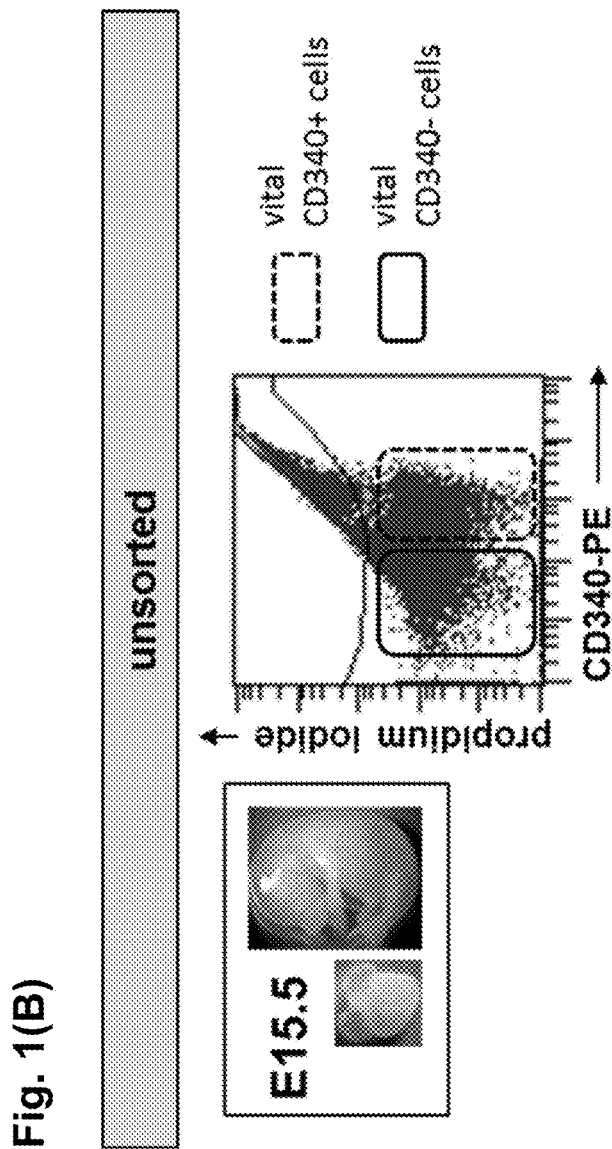

Unexpectedly, the inventors found that the antigens (cell surface markers), CD49f and CD49e are expressed by and define cardiomyocyte subpopulations, i.e. atrial and ventricular cardiomyocytes. Therefore, combined labeling of CD49e or CD49f with an agent, e.g. an antigen binding fragment, binding to a general cardiomyocyte marker (e.g. CD340, CD61, CD146, CD112) allows for enrichment, isolation, detection and/or analysis of atrial and/or ventricular cardiomyocytes from mixed cell populations.

The use of only an antigen-binding fragment, specific for the antigen CD49e or CD49f is sufficient for enrichment, isolation, detection and/or analysis of atrial and/or ventricular cardiomyocytes from a sample containing only cardiomyocytes (e.g. a pre-enriched sample). Removal of non-cardiomyocytes from a mixed sample comprising cardiomyocytes and non-cardiomyocytes (resulting in a pre-enriched sample) can be performed by labeling the non-cardiomyocytes with combinations of antigen-binding fragments specific for cell surface markers of non-cardiomyocytes selected from the group consisting of surface markers Sca-1, CD15, CD31, CD38, CD45, CD49b, CD49d, CD54, CD66a, CD73, CD90.1, CD90.2, CD105, CD117, CD138, CD140a, CD140b, CD184, CD326, provided that for PSC-derived non-cardiomyocytes at least 1 cell surface marker is CD31, CD66a, CD38, CD49b, Sca-1, or CD105 and at least 1 cell surface marker is CD326 or CD15, or provided that for neonatal non-cardiomyocytes at least 1 cell surface marker is CD31, CD105, or CD146 and that the other cell surface markers are CD45, CD51 and CD90.2.

The present invention discloses that CD49e and CD49f are cell surface markers for cardiomyocyte subpopulations. We found high expression of CD49e (CD49e$^{high}$) and weak expression of CD49f (CD49f$^{low}$) on ventricular cardiomyocytes, whereas CD49f is strongly expressed (CD49f$^{high}$) and CD49e is weakly expressed (CD49e$^{low}$) on atrial cardiomyocytes. In a first aspect the present invention provides the use of antigens CD49e and/or CD49f as selection markers (positive selection markers) for enrichment, isolation, detection and/or analysis of atrial and/or ventricular cardiomyocytes. Although both markers are expressed on both subpopulations, they can be differentiated by the strength of expression of the markers, respectively. Any method known to the skilled person in the art, which allows measurement of differentiation of expression strength of surface markers on cells may be suited for the use of antigens CD49e and/or CD49f for enrichment, isolation, detection and/or analysis of cardiomyocyte subpopulations as intended in the present invention. A standard technology, which allows for differentiation of intensities of signals which correlate to the expression level of the protein of the cells is the flow cytometry technology such as FACS®.

In a further aspect the present invention provides a method for enrichment, isolation, detection and/or analysis of atrial and/or ventricular cardiomyocytes from a sample comprising cardiomyocytes, the method comprising the steps
a) contacting said mixed sample
  i) with an antigen-binding fragment specific for the CD49e antigen coupled to a fluorophore, thereby stronger labeling (CD49e$^{high}$) the ventricular cardiomyocytes of said sample than the atrial cardiomyocytes (CD49e$^{low}$) of said sample, or
  ii) with an antigen-binding fragment specific for the CD49f antigen coupled to a fluorophore, thereby stronger labeling (CD49f$^{high}$) the atrial cardiomyocytes of said sample than the ventricular cardiomyocytes (CD49f$^{low}$) of said sample,
b) contacting said sample with an agent which allows specific labeling of cardiomyocytes, thereby co-labeling the cardiomyocytes
c) enriching, isolating, detecting and/or analysing said co-labeled cells by determining a level of CD49e and/or CD49f protein expression on the cell surface of said co-labeled cells, wherein CD49e$^{high}$ or CD49f$^{low}$ expression is indicative of ventricular cardiomyocytes and CD49e$^{low}$ or CD49f$^{high}$ expression is indicative of atrial cardiomyocytes.

The enrichment, isolation, detection and/or analysis of said co-labeled cells by determining a level of CD49e and/or CD49f protein expression on the cell surface of said co-labeled cells may be performed e.g. by flow cytometry.

The agent which allows specific labeling of cardiomyocytes may be e.g. an antigen-binding fragment specific for a general cardiomyocyte cell surface marker coupled to a fluorophore or any other agent enabling specific labeling of cardiomyocytes, e.g. a dye specific for mitochondria such as the cell-permeant MitoTracker® Red, cardiomyocyte-specific DNA or RNA molecules or molecular beacons introduced into individual cells or a population of cells, voltage-sensitive dyes like substituted aminonaphthylethenylpyridinium dyes.

The antigen-binding fragment specific for a cardiomyocyte cell surface marker is selected from the group consisting of cell surface markers CD61, CD146, CD112 and CD340.

More preferentially, the antigen-binding fragment specific for a cardiomyocyte cell surface marker is CD340. Antigen CD61 is a specific cell surface marker for mouse pluripotent stem cell-derived cardiomyocytes. Antigen CD146 is a specific cell surface marker for embryonic mouse heart and mouse pluripotent stem cell-derived cardiomyocytes. Antigen CD112 is a specific cell surface marker for embryonic mouse heart cardiomyocytes. Antigen CD340 is a specific cell surface marker for mouse heart cardiomyocytes, mouse pluripotent stem cell-derived cardiomyocytes, human pluripotent stem cell-derived cardiomyocytes.

The sample comprising cardiomyocytes is any cell comprising sample which comprises cardiomyocytes and non-cardiomyocytes such as a heart preparation, an in vitro culture comprising tissue cell- or cell line- or adult stem cell- or pluripotent stem cell-derived cardiomyocytes.

The coupling of the fluorophore to the antigen binding fragment may be direct or indirect, e.g. via biotin-streptavidin interaction. The antigen-binding fragment may be an antibody or fragment thereof. The atrial and/or ventricular cardiomyocytes may be mammalian cells; preferentially they are murine or human cells. Contacting of the sample comprising cardiomyocytes with an antigen-binding fragment specific for the CD49e or CD49f antigen and with an agent, which allows specific labeling of cardiomyocytes may be performed simultaneously or subsequently.

In another aspect the present invention provides a method for enrichment, isolation, detection and/or analysis of atrial and/or ventricular cardiomyocytes from a sample, which is pre-enriched for cardiomyocytes, the method comprising the steps
a) contacting said pre-enriched sample
  i) with an antigen-binding fragment specific for the CD49e antigen coupled to a tag, thereby stronger labeling (CD49ehigh) the ventricular cardiomyocytes of said pre-enriched sample than the atrial cardiomyocytes (CD49elow) of said pre-enriched sample, or
  ii) with an antigen-binding fragment specific for the CD49f antigen coupled to a tag, thereby stronger labeling the atrial cardiomyocytes (CD49fhigh) of said pre-enriched sample than the ventricular cardiomyocytes (CD49flow) of said pre-enriched sample,
b) enriching, isolating, detecting and/or analysing the labeled cells of said pre-enriched sample by determining a level of CD49e and/or CD49 f protein expression on the surface of said labeled cells, wherein CD49ehigh or CD49flow expression is indicative of ventricular cardiomyocytes and CD49elow or CD49fhigh is indicative of atrial cardiomyocytes.

The enrichment, isolation, detection and/or analysis of said labeled cells by determining a level of CD49e and/or CD49f protein expression on the cell surface of said labeled cells may be performed e.g. by flow cytometry. The cells isolated in step b) may be the atrial and/or ventricular cardiomyocytes. The antigen-binding fragment may be an antibody or fragment thereof. The atrial and/or ventricular cardiomyocytes may be mammalian cells; preferentially they are murine or human cells. The coupling of the tag to the antigen binding fragment may be direct or indirect, e.g. via biotin-streptavidin interaction.

Said sample, which is pre-enriched for cardiomyocytes, may be generated by a cell depleting method. The cell depleting method may comprise the steps I) contacting a non-enriched sample comprising non-cardiomyocytes and cardiomyocytes with combinations of antigen-binding fragments specific for cell surface markers of non-cardiomyocytes coupled to tags, thereby labeling the non-cardiomyocytes, II) isolating the non-labeled cardiomyocytes of said non-enriched sample.

Such a cell depleting method may be e.g. a flow cytometry method or a magnetic cell separation method. But any other method which is suitable for pre-enrichment of cardiomyocytes from the sample comprising cardiomyocytes and other cells may be employed for pre-enrichment. Such another method may be e.g. Percoll® gradient centrifugation or use of specific media promoting survival of cardiomyocytes (e.g. lactate enriched media).

Combinations of antigen-binding fragments specific for surface markers of non-cardiomyocytes may be selected from the group consisting of surface markers Sca-1, CD15, CD31, CD38, CD45, CD49b, CD49d, CD54, CD66a, CD73, CD90.1, CD90.2, CD105, CD117, CD138, CD140a, CD140b, CD184, CD326 with the proviso that for PSC-derived non-cardiomyocytes at least 1 cell surface marker is CD31, CD66a, CD38, CD49b, Sca-1, or CD105 and at least 1 cell surface marker is CD326 or CD15, or with the proviso that for neonatal non-cardiomyocytes at least 1 cell surface marker is CD31, CD105, or CD146 and at the other cell surface markers are CD45, CD51 and CD90.2. Said tag may be e.g. a fluorophore, a hapten such as biotin or a bead. The bead may be e.g. a magnetic bead, e.g. a paramagnetic microbead usable e.g. in the MACS® technology (Miltenyi Biotec GmbH, Germany).

Said isolation of said labeled cells may be performed e.g. by flow cytometry technology such as FCAS® (BD Biosciences) or a magnetic cell separation technology such as MACS® (Miltenyi Biotec GmbH, Germany).

Contacting of a mixed sample comprising cardiomyocytes and non-cardiomyocytes with antigen-binding fragments specific for surface markers of non-cardiomyocytes selected from the group consisting of surface markers Sca-1, CD15, CD31, CD38, CD45, CD49b, CD49d, CD54, CD66a, CD73, CD90.1, CD90.2, CD105, CD117, CD138, CD140a, CD140b, CD184, CD326, with the proviso that for PSC-derived non-cardiomyocytes at least 1 cell surface marker is CD31, CD66a, CD38, CD49b, Sca-1, or CD105 and at least 1 cell surface marker is CD326 or CD15, or with the proviso that for neonatal non-cardiomyocytes at least 1 cell surface marker is CD31, CD105, or CD146 and at the other cell surface markers are CD45, CD51 and CD90.2, and with an antigen-binding fragment specific for the CD49e or CD49f antigen can be performed simultaneously or subsequently.

In a further aspect the present invention provides a substantially pure cardiomyocyte subpopulation composition. The composition may be a substantially pure composition of atrial cardiomyocytes or the composition may be a substantially pure composition of ventricular cardiomyocytes. The substantially pure composition of atrial cardiomyocytes may be obtained by the use of the marker CD49f ($CD49f^{high}$) or CD49e ($CD49e^{low}$) as disclosed herein or by the methods disclosed herein. The substantially pure composition of ventricular cardiomyocytes may be obtained by the use of the marker CD49e ($CD49e^{high}$) or CD49f ($CD49f^{low}$) as disclosed herein or by the methods disclosed herein.

In another aspect the present invention provides a pharmaceutical composition comprising a substantially pure atrial or ventricular cardiomyocytes composition.

In another aspect the present invention provides the use of the cell surface marker CD61 as a selection marker (positive selection marker) for enrichment, isolation, detection and/or analysis of mouse pluripotent stem cell-derived cardiomyocytes. Mouse stem cell derived cardiomyocytes may be generated by methods as described in example 4.

In another aspect the present invention provides the use of the cell surface marker CD146 as a selection marker (positive selection marker) for enrichment, isolation, detection and/or analysis of embryonic mouse heart and mouse pluripotent stem cell-derived cardiomyocytes. Embryonic mouse heart and mouse pluripotent stem cell-derived cardiomyocytes may be generated by methods as described in examples 1-4.

In another aspect the present invention provides the use of the cell surface marker CD112 as a selection marker (positive selection marker) for enrichment, isolation, detection and/or analysis of embryonic mouse heart cardiomyocytes. Embryonic mouse heart cardiomyocytes may be generated by methods as described in examples 1-3.

In another aspect the present invention provides a method for enrichment (or pre-enrichment) of cardiomyocytes from a sample comprising cardiomyocytes and non-cardiomyocytes, the method comprising I) contacting said sample comprising non-cardiomyocytes and cardiomyocytes with combinations of antigen-binding fragments specific for cell surface markers of non-cardiomyocytes coupled to tags, thereby labeling the non-cardiomyocytes, II) isolating the non-labeled cardiomyocytes of said non-enriched sample, wherein said combinations of antigen-binding fragments specific for cell surface markers of non-cardiomyocytes are selected from the group consisting of surface markers Sca-1, CD15, CD31, CD38, CD45, CD49b, CD49d, CD54, CD66a, CD73, CD90.1, CD90.2, CD105, CD117, CD138, CD140a, CD140b, CD184, CD326, with the proviso that for PSC-derived non-cardiomyocytes at least 1 cell surface marker is CD31, CD66a, CD38, CD49b, Sca-1, or CD105 and at least 1 cell surface marker is CD326 or CD15, or with the proviso that for neonatal non-cardiomyocytes at least 1 cell surface marker is CD31, CD105, or CD146 and at the other cell surface markers are CD45, CD51 and CD90.2.

The cells achieved by the methods of the present invention can be cultured analyzed and/or transplanted after enrichment according to all methods known to the person skilled in the art.

DEFINITIONS

Unless defined otherwise, technical and scientific terms used herein have the same meaning as commonly understood by one of ordinary skill in the art to which this invention belongs.

The term "sample" as used herein refers to a sample comprising cardiomyocytes and non-cardiomyocytes in any ratio or a mixture of cardiomyocyte subpopulations, like atrial and ventricular cardiomyocytes. Preferentially, the cells are viable. Viability of cells is achieved by using the cell surface markers of the present invention. The sample can also comprise fixed cells, which may be used for subsequent nucleic acid, organelle or protein extraction. The samples may be from humans or animals, especially mammals including but not limited to mouse, rats, pigs, cattle, dog, monkey. Tissue derived from the heart, e.g. whole heart tissue or special heart regions, any cell composition-derived, preferentially embryonic stem (ES) cells or induced pluripotent stem (iPS) cell derived cells comprising cardiomyocyte subpopulations can be used. The term "mixed sample" as used herein refers specifically to a sample comprising cardiomyocytes and non-cardiomyocytes in any ratio or a mixture of cardiomyocyte subpopulations, like atrial and ventricular cardiomyocytes as can be obtained e.g. by a dissociated heart tissue preparation or by derivation of cardiomyocytes from other cell-types, e.g. from stem cells by inductive stimuli e.g. small molecules, cytokines, growth factors, antibiotics or overexpression of selected genes or RNAs. The term "sample which is pre-enriched for cardiomyocytes" refers to a sample, which is enriched for cardiomyocytes. The enrichment may be performed by any method known in the art, which allows enrichment of specific cell populations. Such methods are e.g. cell depleting methods using magnetic cell separation (untouched fraction) or FACS (surface marker-dependent or surface marker independent (mitochondria, molecular beacons, molecular reporters) or other surface marker-independent experimental procedures such as physical separation based on size (cardiomyocytes accumulate in a specific layer of a Percoll gradient) and use of special media like glucose-depleted media containing abundant levels of lactate.

The invention is illustrated mainly by isolating cardiomyocyte subpopulations from dissociated mouse heart tissue. However, it encompasses isolation of atrial and/or ventricular cardiomyocytes from any mammalian mixed cell population in general using single antigen binding fragments such as antibodies or combinations thereof as described herein. Exemplary it is described in Example 4 that mouse and human pluripotent stem cell-derived cardiomyocytes are labeled by the same antigens as identified in dissociated mouse heart tissue. All procedures of the embodiments of the present invention and the compositions obtainable by the methods can also be from human origin or any other species than mouse.

The term "marker" as used herein refers to a cell antigen that is specifically expressed by a certain cell type. Preferentially, the marker is a cell surface marker, so that enrichment, isolation and/or detection of living cells can be performed. The markers may be positive selection markers such as CD49e and/or CD49f as used herein or may be negative selection markers such as Sca-1, CD15, CD31, CD38, CD45, CD49b, CD49d, CD54, CD66a, CD73, CD90.1, CD90.2, CD105, CD117, CD138, CD140a, CD140b, CD184, CD326 as used herein. Cell antigens that are expressed intracellularly, e.g. structural or muscle proteins or transcription factors are analytical markers used to identify cardiomyocytes and/or subpopulations thereof, but cannot be used for enrichment of viable cells.

The term "$low$" refers to a level of expression of the respective molecules, such as the surface markers CD49e, CD49f or CD340, by a particular cell or population of cells within a sample that is low when compared to the level of expression of that molecule by the population of cells comprising the whole of the sample being analyzed. For example, $CD49f^{low}$ refers to a level of expression of CD49f by a particular cell or population of cells within the sample that is low when compared to the level of expression of CD49f by the population of cells comprising the whole of the sample being analyzed. More particularly, the term "low" may refer to a distinct population of cells that expresses a particular molecule at a level that is lower than that expressed by one or more other distinct populations within a sample. The term "$high$" has a corresponding meaning Additionally, the term "stronger expressed" as used herein correlates with the term "$high$" and the terms "weaker expressed" as used herein or "lower expressed" as used herein correlate with the term "$low$". For example, CD49e is stronger expressed on ventricular cardiomyocytes ($CD49e^{high}$) than on atrial cardiomyocytes ($CD49e^{low}$), i.e. there are more CD49e molecules on the cell surface of ventricular than atrial cardiomyocytes. Therefore, labeling of both cardiomyocyte subpopulations within a sample leads to a stronger labeling (e.g. fluorescence labeling) of ventricular than atrial cardiomyocytes. The ventricular cardiomyocyte subpopulation is therefore defined as $CD49e^{high}$, the atrial cardiomyocyte subpopulation as $CD49e^{low}$. Exemplary the higher expression of CD49e in ventricular cardiomyocytes compared to the lower expression of CD49e in atrial cardiomyocytes is shown in a flow cytometry analysis of FIG. 2 B. Corresponding is the situation of the expression level for CD49f as shown exemplary in FIGS. 2 B, 3, 4 A-C.

The term "expression" as used herein refers interchangeably to expression of a gene or gene product, including the encoded protein. Expression of a gene product may be determined e.g. by an immunoassay using antibodies that bind with the protein. For example, a well-suited technology for determining the level of proteins, e.g. the cell surface proteins CD49e and CD49f, is the flow cytometry technology. Alternatively, expression of a gene may be determined by e.g. measurement of mRNA levels.

The term "cardiomyocyte" or "cardiomyocytes" as used herein refers to sarcomere-containing striated muscle cells, naturally found in the mammalian heart, as opposed to skeletal muscle cells. Cardiomyocytes are characterized by the expression of specialized molecules e.g. proteins like myosin heavy chain, myosin light chain, cardiac alpha-actinin. Cardiomyocytes can as well be generated from other cell types by inductive cues, e.g. special media, small molecules, growth factors, cytokines, overexpression of selected genes or RNAs. The term "cardiomyocyte" as used herein is an umbrella term comprising any cardiomyocyte subpopulation or cardiomyocyte subtype, e.g. atrial, ventricular and pacemaker cardiomyocytes.

The term "non-cardiomyocyte" as used herein refers to any cell or population of cells in a cell preparation not fulfilling the criteria of a "cardiomyocyte" as defined and used herein.

The terms "cardiomyocyte subpopulation" or "cardiomyocyte subtype" are used interchangeably and refer to atrial or ventricular cardiomyocytes or both. Atrial cardiomyocytes are naturally present in the heart atria, whereas ventricular cardiomyocytes are naturally present in the heart ventricles. Additionally, atrial and ventricular cardiomyocytes may as well be generated from other cells by inductive cues, e.g. special media, small molecules, growth factors, cytokines, overexpression of selected genes or RNAs. Atrial cardiomyocytes are characterized by any criteria defined herein for cardiomyocytes, but are additionally specified by expression of certain intracellular molecules, like proteins encoded by certain genes, e.g. Myl7, Fgf12, Sln, Gja5, Nppa, Tbx5.

Ventricular cardiomyocytes are characterized by any criteria defined herein for cardiomyocytes, but are additionally specified by expression of certain intracellular molecules, like proteins encoded by certain genes, e.g. Hey2, Irx4, Lbh, Myh7.

The terms "unmodified atrial and/or ventricular cardiomyocytes" or "unmodified cardiomyocyte subpopulation" as used herein refer to a respective cell or population of cells within a sample that was neither transiently nor permanently manipulated or modified e.g. by transfection of molecules, e.g. DNA or RNA-containing molecules, molecular beacons, voltage sensitive dyes or mitochondria-specific dyes.

The cells enriched, isolated, detected and/or analyzed by the method of the present invention may be viable, unmodified atrial and/or ventricular cardiomyocytes. But the cells enriched, isolated, detected and/or analyzed by the method of the present invention may also be viable modified or manipulated atrial and/or ventricular cardiomyocytes. But the cells enriched, isolated, detected and/or analyzed by the method of the present invention may also be fixed unmodified or modified/manipulated atrial and/or ventricular cardiomyocytes.

The term "removal/depletion" as used herein refers to a process of a negative selection that separates desired cardiomyocytes (untouched) from the undesired non-cardiomyocytes e.g. by labeling with antigen-binding fragments specific for non-cardiomyocytes as defined and used herein or by the use of physical depletion methods, e.g. Percoll gradient centrifugation or by the use of special media (e.g. glucose depleted lactate rich media) or by use of DNA or RNA molecules or molecular beacons thereby specifically labeling non-cardiomyocytes and enabling their depletion by a cell separation procedure, e.g. magnetic cell sorting or FACS.

The term "tag" as used herein refers to the coupling of the antigen-binding fragment, e.g. an antibody or fragment thereof, to other molecules, e.g. particles, fluorophores, haptens like biotin, or larger surfaces such as culture dishes and microtiter plates. In some cases the coupling results in direct immobilization of the antigen-binding fragment, e.g. if the antigen-binding fragment is coupled to a larger surface of a culture dish. In other cases this coupling results in indirect immobilization, e.g. an antigen-binding fragment coupled directly or indirectly (via e.g. biotin) to a magnetic bead is immobilized if said bead is retained in a magnetic field. In further cases the coupling of the antigen-binding fragment to other molecules results not in a direct or indirect immobilization but allows for enrichment, separation, isolation, and detection of cells according to the present invention, e.g. if the antigen-binding fragment is coupled to a fluorophore which then allows discrimination of stronger labeled cells, weaker labeled cells, and non-labeled cells, e.g. via flow cytometry methods, like FACSorting, or fluorescence microscopy.

The term "particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a lyophilised state prior to use in the present invention. The lyophilized particle is then reconstituted in convenient buffer before contacting the sample to be processed regarding the present invention.

The term "magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The term "antigen-binding fragment" as used herein refers to any moiety that binds preferentially to the desired target molecule of the cell, i.e. the antigen.

The term "moiety" comprises, e.g., an antibody or antibody fragment.

The term "antibody" as used herein refers to polyclonal or monoclonal antibodies, which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies).

The term "antibody" comprises both intact molecules and antibody fragments, such as Fab, Fab', F(ab')2, Fv and single-chain antibodies. Additionally, the term "antigen-binding fragment" includes any moiety other than antibodies or antibody fragments that binds preferentially to the desired target molecule of the cell. Suitable moieties include, without limitation, oligonucleotides known as aptamers that bind to desired target molecules (Hermann and Patel (2000) Science 289:820-825), carbohydrates, lectins or any other antigen binding protein (e.g. receptor-ligand interaction). The linkage (coupling) between antibody and tag or particle can be covalent or non-covalent. A covalent linkage can be, e.g. the linkage to carboxyl-groups on polystyrene beads, or to $NH_2$ or $SH_2$ groups on modified beads. A non-covalent linkage is e.g. via biotin-avidin or a fluorophore-coupled-particle linked to anti-fluorophore antibody. Methods for coupling antibodies to particles, fluorophores, haptens like biotin or larger surfaces such as culture dishes are well known to the skilled person in the art.

For removal, enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells.

An especially potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies can be directly coupled to magnetic polystyrene particles like Dynal® M 450 or similar magnetic particles and used e.g. for cell separation. The Dynabeads® technology is not column based, instead these magnetic beads with attached cells enjoy liquid phase kinetics in a sample tube, and the cells are isolated by placing the tube on a magnetic rack. However, in a preferred embodiment for enriching, sorting and/or detecting cardiomyocyte subpopulations from a sample containing cardiomyocytes according the present invention monoclonal antibodies are used in conjunction with colloidal superparamagnetic microparticles having an organic coating by e.g. polysaccharides (Magnetic-activated cell sorting (MACS®) technology (Miltenyi Biotec, Bergisch Gladbach, Germany)). These particles (nanobeads or MicroBeads®) can be either directly conjugated to monoclonal antibodies or used in combination with anti-immunoglobulin, avidin or anti-hapten-specific MicroBeads®. The MACS technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s). In case of a positive selection the cells expressing the antigen(s) of interest, which attached to the magnetic column, are washed out to a separate vessel, after removing the column from the magnetic field. In case of a negative selection the antibody used is directed against surface antigen(s), which are known to be present on cells that are not of interest. After application of the cells/magnetic nanoparticles solution onto the column the cells expressing these antigens bind to the column and the fraction that goes through is collected, as it contains the cells of interest. As these cells are non-labeled by an antibody coupled to nanoparticles, they are "untouched". The procedure can be performed using direct magnetic labeling or indirect magnetic labeling. For direct labeling the specific antibody is directly coupled to the magnetic particle. Indirect labeling is a convenient alternative when direct magnetic labeling is not possible or not desired. A primary antibody, a specific monoclonal or polyclonal antibody, a combination of primary antibodies, directed against any cell surface marker can be used for this labeling strategy. The primary antibody can either be unconjugated, biotinylated, or fluorophore-conjugated. The magnetic labeling is then achieved with anti-immunoglobulin MicroBeads®, anti-biotin MicroBeads®, or anti-fluorophore MicroBeads®. The method of the present invention allows for both the direct magnetic labeling and the indirect magnetic labeling with the aim of a) removal of non-cardiomyocytes from a mixed cell population or b) enrichment of cardiomyocytes and cardiomyocyte subtypes from a mixed cell population (see Examples 1-4).

The term "agent" as used herein refers to any molecule, which allow specific labeling of the target cells, i.e. the cardiomyocytes within the method of the present invention. The agent can be e.g. an antigen binding fragment specific for a cardiomyocyte cell surface marker, a dye specific for mitochondria, cardiomyocyte-specific DNA, or RNA molecules or molecular beacons introduced into individual cells or a population of cells, or voltage-sensitive dyes like substituted aminonaphthylethenylpyridinium dyes.

The term "substantially pure composition of atrial or ventricular cardiomyocytes" as used herein refers to a cell composition containing at least 70%, more preferentially at least 90%, most preferentially at least 95% of alpha-actinin positive cells in the target cell fraction. Depending on use of either the CD49e or the CD49f antigen for enrichment as well as selecting for either the $CD49e^{high}$ or $CD49f^{high}$ or $CD49e^{low}$ or $CD49f^{low}$ subpopulation within the alpha-actinin positive cell population, the ratio of atrial cardiomyocytes is at least 70%, the ratio of ventricular cardiomyocytes is at least 90%. Normally, cardiomyocytes are integrated in a network of different cell types in vivo. To make them accessible to enrichment and sorting techniques the tissue has to be dissociated before use of such methods. In the present invention, heart tissue or pluripotent stem cell-derived embryoid bodies or monolayer cell culture are enzymatically treated using e.g. the MACS® Neonatal Heart Dissociation Kit or the MACS® Embryoid Body Dissociation Kit (Miltenyi Biotec). The cell composition is further mechanically dissociated manually or with an instrument that allows automated tissue dissociation, e.g. gentleMACS™ Dissociator (Miltenyi Biotec). Other methods that allow generation of a viable single cell suspension from heart tissue or embryoid bodies or monolayer cell culture cells can also be used and are well known by the person skilled in the art.

The cardiomyocytes and/or cardiomyocyte subpopulations obtainable by the methods disclosed herein may be used for subsequent steps such as research, diagnostics, pharmacological or clinical applications known to the person skilled in the art. Purification of cardiomyocyte subpopulations from the variety of other cell types in the heart as well as in pluripotent stem cell differentiation cultures is a prerequisite for molecular, biochemical or electrophysiological in vitro analysis. Cells can be taken into culture using a Medium optimized for this application. In the present invention isolated cells were seeded onto fibronectin-coated multiwell tissue culture plates and maintained in a humidified atmosphere (5% CO2, 95% air) at 37° C. for at least 24 h using DMEM with stable glutamine (Miltenyi Biotec) supplemented with 10% FBS. Such cardiomyocyte subtype cultures can be used to study e.g. cardiac development, cardiomyocyte subtype specification, cardiomyocyte maturation, cardiomyocyte proliferation, cell signaling, or to perform electrophysiological measurements for the investigation of cardiomyocyte electrical activity.

The enriched cardiomyocyte subpopulations can also be used before and/or after cell culturing as a pharmaceutical composition in the therapy, e.g. cellular therapy, or prevention of diseases. The pharmaceutical composition may be transplanted into an animal or human, preferentially a human patient. The pharmaceutical composition can be used for the treatment and/or prevention of diseases in mammals, especially humans, possibly including administration of a pharmaceutically effective amount of the pharmaceutical composition to the mammal. The disease may be any disease, which can be treated and/or prevented through the presence of cardiomyocytes and/or through increasing the concentration of the relevant cells in/at the relevant place, i.e. the heart. The treated and/or preventively treated disease may be any heart disorder, e.g. a disorder characterized by loss of cardiomyocytes as a result of ischemia or acute/chronic inflammation. The treatment may be the transplantation of enriched cardiomyocyte subpopulations to the relevant place of the heart. Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

EMBODIMENTS

Methods which allow for the use of positive or negative selection markers for enrichment, isolation, detection and/or analysis of cells are e.g. magnetic cell separation methods, immunopanning, flow cytometry methods such as FACS®, and FACS sorting. The antigen binding fragments may be labeled with tags such as particles, e.g. magnetic particles, haptens like biotin, or fluorophores. The antigen binding fragments may be immobilized, e.g. by attaching them on the surface of culture dishes or by labeling them with particles such as magnetic beads or fluorophores.

In one embodiment of the present invention the antigen-binding fragment is an anti-CD49e antibody coupled to a fluorophore. The (mixed) sample comprising cardiomyocytes is e.g. a dissociated heart tissue from e.g. a human or murine source or an in vitro cultivated population of cells from e.g. a human or mouse source. For enrichment, isolation, detection and/or analysis of atrial and/or ventricular cardiomyocytes of said sample, firstly said sample is labeled with said anti-CD49e antibody coupled to a fluorophore (positive selection marker for cardiomyocyte subtypes). The ventricular cardiomyocytes are stronger labeled by said antibody (CD49e$^{high}$) compared to the atrial cardiomyocytes (CD49e$^{low}$) of said sample due to higher expression level of CD49e on the cell surface of ventricular cardiomyocytes. Secondly, said sample is co-labeled with an antigen-binding fragment specific for a cardiomyocyte cell surface marker coupled to another fluorophore, e.g. anti-CD340 antibody. Using a flow cytometry device such as FACS®, the double-labeled (co-labeled) cells can be distinguished from non-labeled or unique-labeled cells. In addition, and essentially to the present invention, the stronger labeled ventricular cardiomyocytes (CD49e$^{high}$) can be distinguished from the weaker labeled atrial cardiomyocytes (CD49e$^{low}$) (differentiating between low and high CD49e expression).

Therefore, depending on the strength of labeling of the target cells, i.e. the cardiomyocyte subpopulations, the co-labeled cells can be enriched, isolated, detected and/or analysed. If the ventricular cardiomyocytes are the target cells then the stronger labeled cells (CD49e$^{high}$) are enriched, isolated, detected and/or analysed. If the atrial cardiomyocytes are the target cells then the weaker labeled cells (CD49e$^{low}$) are enriched, isolated, detected and/or analysed. Cultivation of these cells leads to a cardiomyocyte subtype cell population that shows only a low percentage of contaminating non-cardiomyocytes (<5%) (see Example 2).

In another embodiment of the present invention the antigen-binding fragment is an anti-CD49f antibody coupled to a fluorophore. The (mixed) sample comprising cardiomyocytes is e.g. a dissociated heart tissue from e.g. a human or murine source or an in vitro cultivated population of cells from e.g. a human or mouse source. For enrichment, isolation, detection and/or analysis of cardiomyocytes of said sample, firstly said sample is labeled with said anti-CD49f antibody coupled to a fluorophore (positive selection marker for cardiomyocyte subtypes). The atrial cardiomyocytes are stronger labeled (CD49f$^{high}$) by said antibody compared to the ventricular cardiomyocytes (CD49f$^{low}$) of said sample due to higher expression level of CD49f on the cell surface of atrial cardiomyocytes. Secondly, said mixed sample is co-labeled with an antigen-binding fragment specific for a cardiomyocyte cell surface marker coupled to another fluorophore, e.g. anti-CD340 antibody. Using a flow cytometry device such as FACS®, the double-labeled (co-labeled) cells can be distinguished from non-labeled or unique-labeled cells. In addition, and essentially to the present invention, the stronger labeled atrial cardiomyocytes (CD49f$^{high}$) can be distinguished from the weaker labeled ventricular cardiomyocytes (CD49f$^{low}$) (differentiating between low and high CD49f expression). Therefore, depending on the strength of labeling of the target cells, i.e. the cardiomyocyte subpopulations, the co-labeled cells can be enriched, isolated, detected and/or analysed. If the atrial cardiomyocytes are the target cells then the stronger labeled cells (CD49f$^{high}$) are enriched, isolated, detected and/or analysed. If the ventricular cardiomyocytes are the target cells then the weaker labeled cells (CD49f$^{low}$) are enriched, isolated, detected and/or analysed. Cultivation of these cells leads to a cardiomyocyte subtype cell population that shows only a low percentage of contaminating non-cardiomyocytes (<5%) (see e.g. Example 3).

In another embodiment of the present invention the antigen-binding fragment is an anti-CD49e or CD49f antibody coupled to a fluorophore. The (mixed) sample comprising cardiomyocytes is e.g. a dissociated heart tissue from e.g. a human or murine source or an in vitro cultivated population of cells from e.g. a human or mouse source. For enrichment, isolation, detection and/or analysis of cardiomyocytes of said sample, firstly said sample is labeled with said anti-CD49e or CD49f antibody coupled to a fluorophore (positive selection marker for cardiomyocytes). Secondly, said sample is co-labeled with any other agent enabling specific labeling of cardiomyocytes, e.g. a dye specific for mitochondria such as the cell-permeant MitoTracker® Red, cardiomyocyte-specific DNA or RNA molecules or molecular beacons introduced into individual cells or a population of cells, voltage-sensitive dyes like substituted aminonaphthylethenylpyridinium dyes. Using a flow cytometry device such as FACS®, the double-labeled (co-labeled) cells can be distinguished from non-labeled or unique-labeled cells.

In another embodiment of the present invention the antigen-binding fragment is e.g. an anti-CD49e antibody coupled to a tag. The tag may be a fluorophore. The sample is a sample, which is pre-enriched for cardiomyocytes. For enrichment, isolation, detection and/or analysis of cardiomyocyte subtypes of said sample pre-enriched for cardiomyocytes, said sample is labeled with said anti-CD49e antibody coupled to a fluorophore (positive selection marker for cardiomyocytes subtypes). The ventricular cardiomyocytes are stronger labeled (CD49e$^{high}$) by said antibody compared to the atrial cardiomyocytes (CD49e$^{low}$) of said sample due to higher expression level of CD49e on the cell surface of ventricular cardiomyocytes. Using a flow cytometry device such as FACS®, the labeled cells can be distinguished from non-labeled cells. In addition, and essential to the present invention, the stronger labeled ventricular cardiomyocytes (CD49e$^{high}$) can be distinguished from the weaker labeled (CD49e$^{low}$) atrial cardiomyocytes (differentiating between low and high CD49e expressing cells). Therefore, depending on the strength of labeling of the target cells, i.e. the cardiomyocyte subpopulations, the labeled cells can be enriched, isolated, detected and/or analysed. If the ventricular cardiomyocytes are the target cells then the stronger labeled cells (CD49e$^{high}$) are enriched, isolated, detected and/or analysed. If the atrial cardiomyocytes are the target cells then the weaker labeled cells (CD49e$^{low}$) are enriched, isolated, detected and/or analysed. Analog the process is performed using the anti CD49f antibody.

In another embodiment of the present invention the antigen-binding fragment is e.g. an anti-CD49f antibody coupled to a tag. The tag may be a magnetic particle such as a MicroBead® (Miltenyi Biotec GmbH). The sample is a sample, which is pre-enriched for cardiomyocytes. For enrichment, isolation, detection and/or analysis of cardiomyocytes of said sample, firstly said sample is labeled with said anti-CD49f antibody coupled to a MicroBead (positive selection marker for cardiomyocyte subtypes). The atrial cardiomyocytes are stronger labeled (CD49f$^{high}$) by said antibody compared to the ventricular cardiomyocytes (CD49f$^{low}$) of said sample due to higher expression level of CD49f on the cell surface of atrial cardiomyocytes. The concentration of anti-CD49f antibodies coupled to the magnetic bead used to label the cells of said sample is chosen for concentrations which are sufficiently high to label the atrial cardiomyocytes (CD49f$^{high}$) but are sufficiently low to lead to no detectable labeling (or at least insignificant labeling) of the ventricular cardiomyocytes ($CD49f^{low}$). The target cells, in this case the atrial cardiomyocytes, can be enriched, isolated, detected and/or analysed by using a magnetic cell separation technology such as MACS® technology. Analog the process is performed using the anti CD49e antibody. Using the anti CD49e antibody the target cells are the ventricular cardiomyocytes, that can be enriched, isolated, detected and/or analysed by using a magnetic cell separation technology such as MACS® technology.

The pre-enrichment of cardiomyocytes of the above-mentioned enriched samples may be performed by any method known in the art, which allows enrichment of specific cell types. Such methods are e.g. surface marker-independent experimental procedures such as physical separation based on size (cardiomyocytes accumulate in a specific layer of a Percoll gradient) or by the use of special media (e.g. glucose depleted, lactate rich media) or by use of DNA or RNA molecules or molecular beacons thereby specifically labeling non-cardiomyocytes and enabling their depletion by a cell separation procedure, e.g. magnetic cell sorting or FACS.

In another embodiment of the present invention said pre-enriched sample is generated by a cell depletion method. A non-enriched sample containing non-cardiomyocytes and cardiomyocytes is contacted with combinations of antigen-binding fragments specific for cell surface markers of non-cardiomyocytes coupled to tags, thereby labeling the non-cardiomyocytes. Said combinations of antigen-binding fragments specific for surface markers of non-cardiomyocytes are selected from the group consisting of surface markers Sca-1, CD15, CD31, CD38, CD45, CD49b, CD49d, CD54, CD66a, CD73, CD90.1, CD90.2, CD105, CD117, CD138, CD140a, CD140b, CD184, CD326 with the proviso that for PSC-derived non-cardiomyocytes at least 1 cell surface marker is CD31, CD66a, CD38, CD49b, Sca-1, or CD105 and at least 1 cell surface marker is CD326 or CD15, or with the proviso that for neonatal non-cardiomyocytes at least 1 cell surface marker is CD31, CD105, or CD146 and at the other cell surface markers are CD45, CD51 and CD90.2.

The antigen-binding fragments may be antibodies specific for the above-mentioned antigens. The tag may be a magnetic particle such as a MicroBead (Miltenyi Biotec GmbH). Using a magnetic cell separation technology such as MACS®, the labeled non-cardiomyocytes are retained in a magnetic column but the unlabeled, i.e. untouched cardiomyocytes are in the flow-through. Then the flow-through is the pre-enriched sample. If the tag is a fluorophore, then the separation technology used is e.g. a flow cytometry technology such as FACS®.

In another embodiment of the present invention a substantially pure composition of cardiomyocyte subpopulations, i.e. atrial and/or ventricular cardiomyocytes, is generated. To our knowledge the present invention discloses for the first time the possibility to enrich, isolate, detect and/or analyse substantially pure compositions of cardiomyocyte subpopulations by means of cell surface marker-based methods as disclosed herein. Therefore a substantially pure composition of cardiomyocyte subpopulations is obtainable by the method of the present invention. These compositions may be used for subsequent steps such as research, diagnostics, pharmacological or clinical applications known to the person skilled in the art.

In another embodiment of the present invention a substantially pure pharmaceutical composition of cardiomyocyte subpopulations, i.e. atrial and/or ventricular cardiomyocytes, is generated. The enriched cardiomyocyte subpopulations can be used e.g. before and/or after cell culturing as a pharmaceutical composition in the therapy, e.g. cellular therapy, or prevention of diseases.

The cell separation components necessary to perform the methods disclosed herein may be provided as a kit. Each kit contains the components necessary to perform the separation of desired cells from a sample containing cardiomyocyte subpopulations. A kit for enrichment, isolation and/or detection of cardiomyocyte subpopulations comprises a) an antigen-binding fragment specific for the CD49e or CD49f antigen coupled to a tag; and optionally b) an antigen-binding fragment specific for a cardiomyocyte-specific cell surface marker coupled to a tag; or optionally c) antigen-binding fragments specific for non-cardiomyocytes coupled to a tag. For use in FACSorting the antigen binding fragments are coupled to fluorophores as described herein. For use in magnetic cell sorting the antigen binding fragments are coupled to magnetic particles as described herein. The magnetic particles, e.g. MicroBeads®, of the kit may be in a solution or suspension or they may be in a lyophilized state prior to use in a method of the present invention. The lyophilized particle is then reconstituted in convenient buffer before contacting with the sample containing cardiomyocyte subpopulations to be processed regarding the present invention. The antigen-binding fragment specific for a cardiomyocyte specific cell surface marker may be CD340, CD61, CD112, CD146 or other relevant cardiomyocyte cell surface markers.

EXAMPLES

Example 1

Surface Marker-Based Detection and Isolation of Cardiomyocytes During Murine Heart Development In order to evaluate the expression pattern of CD340 (ErbB2) between embryonic day (E) 11.5 and postnatal day (P) 2, single-cell suspensions of mouse hearts were prepared by manual or automated tissue dissociation. Single cells were co-labeled with APC- or PE-coupled antibodies against CD340 as well as a FITC-coupled antibody against the intracellular cardiomyocyte muscle protein alpha-actinin and analyzed by flow cytometry (FIG. 1(A)). At E11.5, CD340 was expressed on virtually all cells of the isolated murine heart, including all cardiomyocytes. During further development, CD340 was first down-regulated on the non-myocytes resulting in an exclusive detection of CD340 on cardiomyocytes at E15.5. After birth, expression on cardiomyocytes decreased as well (P2).

In order to investigate whether CD340 labeling could serve as a general marker to detect or to isolate immature murine cardiomyocytes, CD340+ cells were purified from single cell suspensions of E15.5 murine hearts by fluorescence-activated cell sorting (FACS) (FIGS. 1(B), 1(C) and 1(D)). Single cells were labeled with a PE-conjugated anti-CD340 antibody and sorting gates were set to propidium iodide (PI) negative, CD340 positive cells (cardiomyocytes) as well as PI negative, CD340 negative cells (non-myocytes). Flow cytometric re-analysis of the fractions revealed a purification of CM up to 95% in the CD340+ fraction (FIG. 1(C)).

Example 2

Figure 2A:
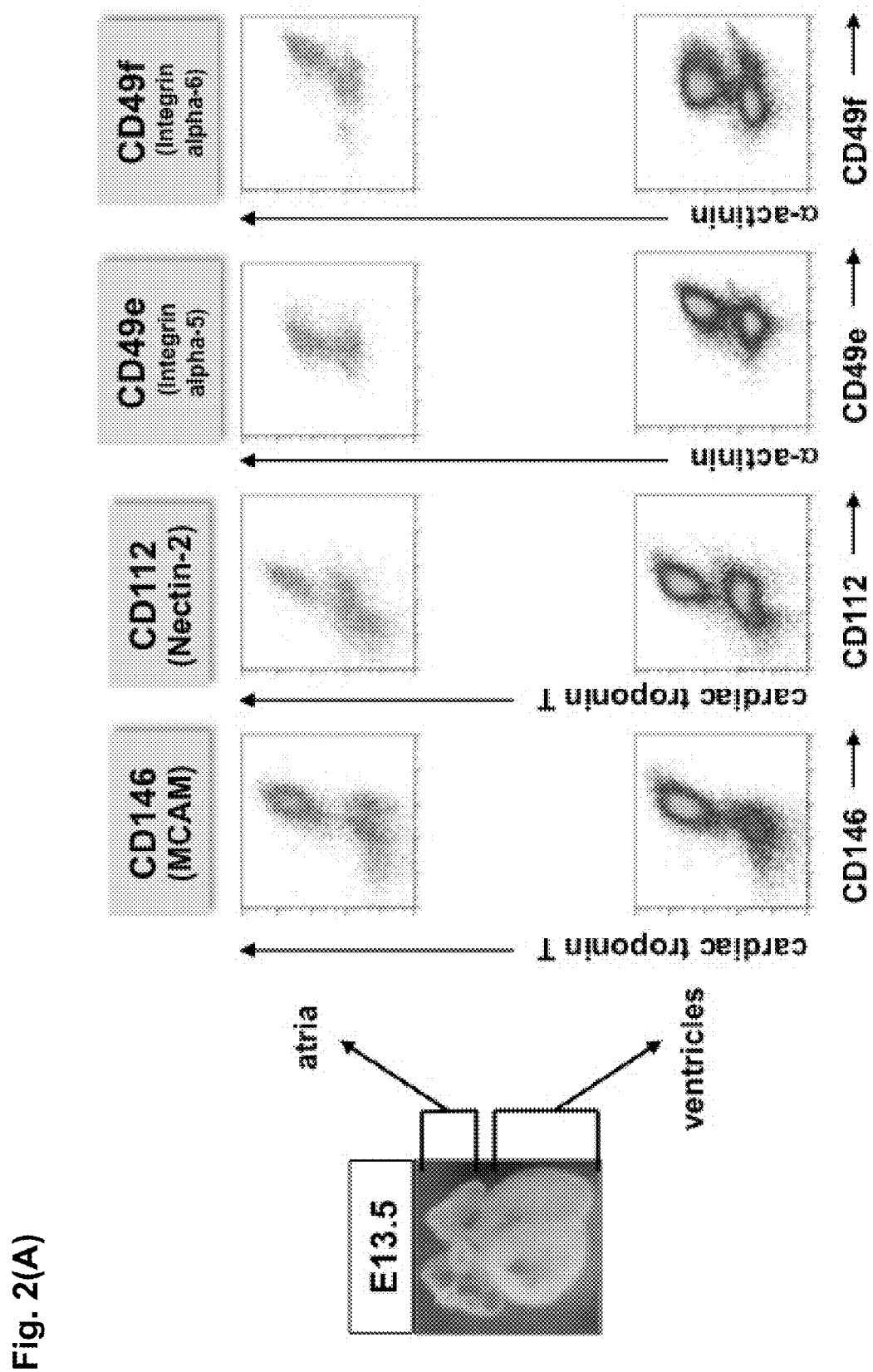
FIGS. 2(A) and 2(B) show differential expression of CD49e and CD49f identified cardiomyocyte subpopulations of murine embryonic hearts (E13.5).

Surface Marker-Based Detection of Cardiomyocyte Subpopulations During Murine Heart Development As a model system to detect atrium- or ventricle-specific cardiomyocyte surface markers we used mechanically dissected mouse hearts into atrial and ventricular cell fractions. Murine E13.5 hearts were isolated, dissected, independently dissociated to form single cell suspensions and screened for surface markers. About 200 antibodies, which were directed against murine surface epitopes, were tested on single cell suspensions. As a result, we identified general cardiomyocyte surface markers, i.e. CD146 and CD112, co-expressed with the intracellular cardiomyocyte markers alpha-actinin or cardiac troponin T (FIG. 2(A)). Surprisingly, the antibody screen identified two antibodies detecting the cell surface antigens CD49e and CD49f as co-expressed with alpha-actinin or cardiac troponin T, but differentially expressed in cardiomyocyte subpopulations from atria and ventricles. The CD49e surface epitope was stronger expressed in the ventricular subpopulation of cardiomyocytes (CD49e$^{high}$) than in the atrial fraction (CD49e$^{low}$). In contrast, the CD49f surface antigen was higher expressed in the atrial subpopulation of cardiomyocytes (CD49f$^{high}$; FIG. 2(A), top row), and weaker expressed in the ventricular subpopulation of cardiomyocytes (CD49f$^{low}$; FIG. 2(A), bottom row).

Figure 2B:
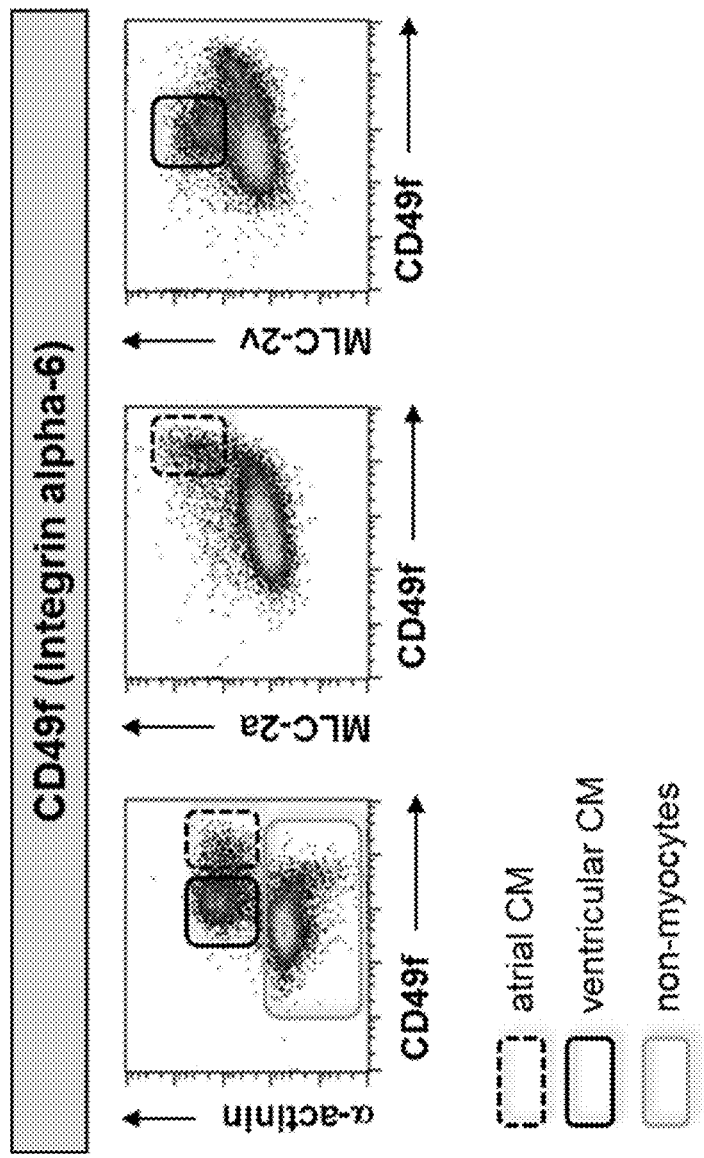

To further investigate the cardiomyocyte expression pattern of CD49f and CD49e on atrial and ventricular cardiomyocytes, single cell suspensions of whole murine hearts (E13.5) were labeled with antibodies against CD49f (FIG. 2(B)) or CD49e (FIG. 2(C)) as well as antibodies against alpha-actinin or against the cardiomyocyte subtype-specific myosin light chains (MLC) 2a and 2v. As shown by flow cytometry, all alpha-actinin+ cells could be divided into a CD49f$^{low}$ and a CD49f$^{high}$ cell population according to fluorescence intensity. CD49f$^{high}$ and CD49f$^{low}$ expression corresponded to MLC-2a and MLC-2v expression, respectively, thereby indicating strong expression in atrial and low expression in ventricular cardiomyocytes. The CD49e expression pattern was opposing to CD49f, with a high intensity on MLC-2v+ cells (CD49e$^{high}$ population) and a lower intensity on MLC-2a+ cells (CD49e$^{low}$ population), respectively, thereby indicating strong expression in ventricular and low expression in atrial cardiomyocytes.

Figure 3:
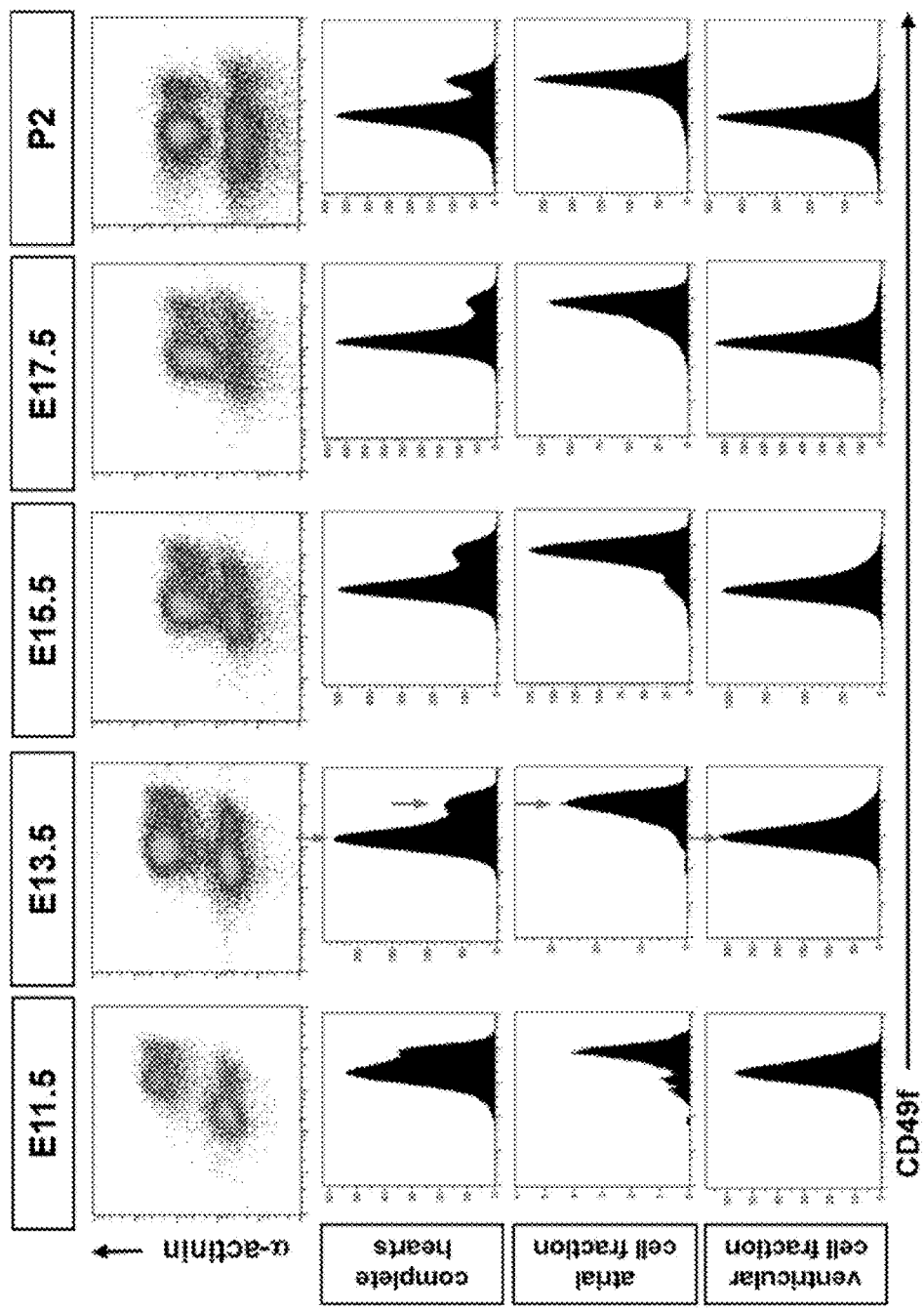
FIG. 3 shows differential expression of alpha-actinin and CD49f identified cardiomyocyte subpopulations of murine hearts as determined by flow cytometry. The cardiomyocyte subpopulations represent complete hearts, the atrial cell fraction, and the ventricular cell fraction. Samples were taken at stages throughout development (E11.5, E13.5, E15.5, E17.5 and P2).

Since we could show that CD49f expression allows discrimination of atrial and ventricular cardiomyocytes in E13.5 murine hearts, we next wanted to characterize this pattern throughout murine heart development (E11.5-P2). Single cell suspensions of complete hearts or mechanically dissected atrial and ventricular tissue fractions were co-labeled with an antibody against CD49f and an antibody against alpha-actinin (FIG. 3). Flow cytometric analysis of the co-expression (density plots, top row) revealed that alpha-actinin+ cells could be divided into a CD49f$^{low}$ and a CD49f$^{high}$ cell population according to fluorescence intensity at all investigated stages. This could also be made clear by histograms of CD49f expression gated on alpha-actinin+ cells which showed two peaks for CD49f expression in complete hearts (gray arrows). Histograms of atrial and ventricular cardiomyocytes, however, resulted in only one respective peak: CD49f$^{high}$ peak for the atrial cardiomyocytes and a CD49f$^{low}$ peak for the ventricular cardiomyocytes.

Example 3

Surface Marker-Based Isolation of Cardiomyocyte Subpopulations from Murine Developing Heart Altogether these findings clearly suggested that the combination of antibodies against a general and a cardiomyocyte subtype-specific surface marker allow the discrimination of atrial and ventricular cardiomyocytes. As shown by flow cytometric analysis of co-labeled single cell suspensions of murine hearts (FIG. 4(A)), atrial cardiomyocytes could either be selectively removed from the mixture of atrial and ventricular cardiomyocytes by isolation of CD340+/CD49f$^{low}$ cells or could be selectively enriched by isolation of CD340+/CD49f$^{high}$ cells. This was true for pre-natal (E15.5, top row) as well as for postnatal hearts (P2, bottom row).

For neonatal murine hearts, we also found the option to combine an antibody-based removal of non-myocytes with a cardiomyocyte subtype-specific surface marker to discriminate atrial from ventricular cardiomyocytes and subsequently isolate either cardiomyocyte subpopulation. Single cell suspensions of murine hearts (P2) were labeled with a mixture of microbead-coupled antibodies against surface markers that were specifically expressed on non-myocytes of the neonatal heart, i.e. CD31, CD45, CD51, CD90.2 (not shown). Magnetic cell separation led to cardiomyocyte purities over 95%. Co-labeling of the enriched cardiomyocytes allowed again for the flow cytometric discrimination of atrial (CD49f$^{high}$ cells) and ventricular cardiomyocytes (CD49f$^{low}$ cells).

Figure 4C:
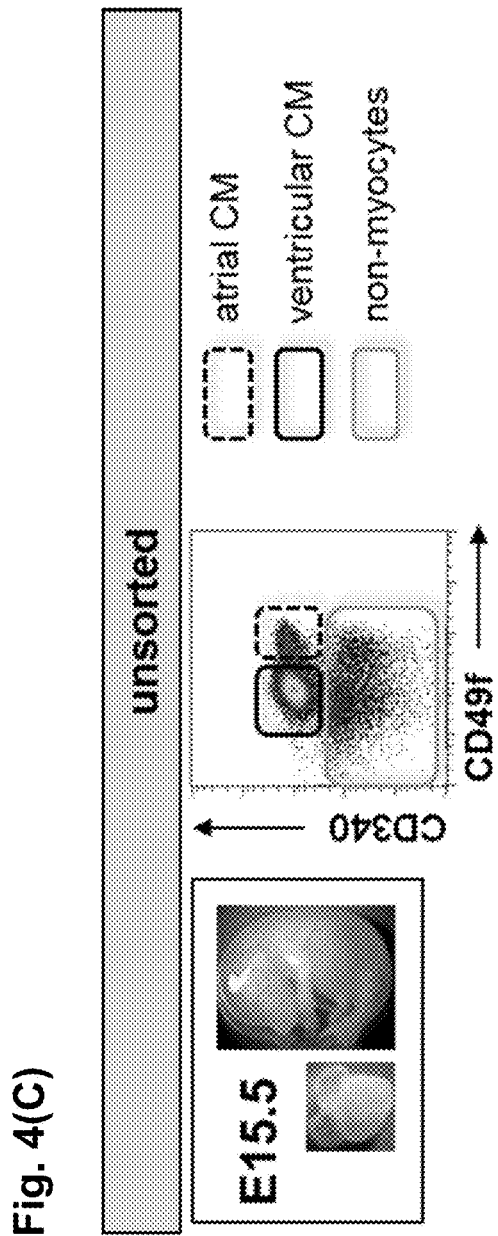
FIGS. 4(C), 4(D), and 4(E) show the results of fluorescence-activated cell sorting (FACS) of murine hearts conducted using the surface markers CD340 and CD49f (E15.5).
Figure 4D:
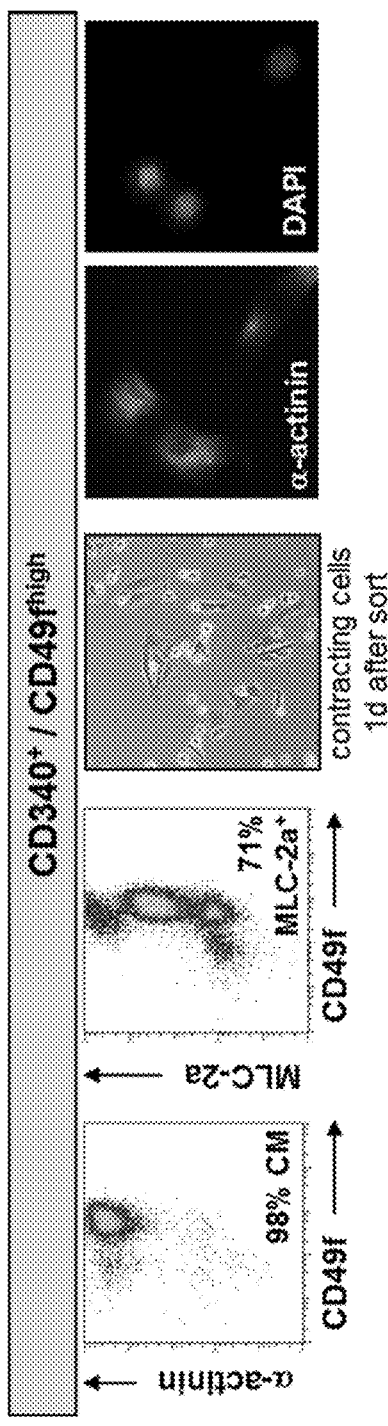
Figure 4E:
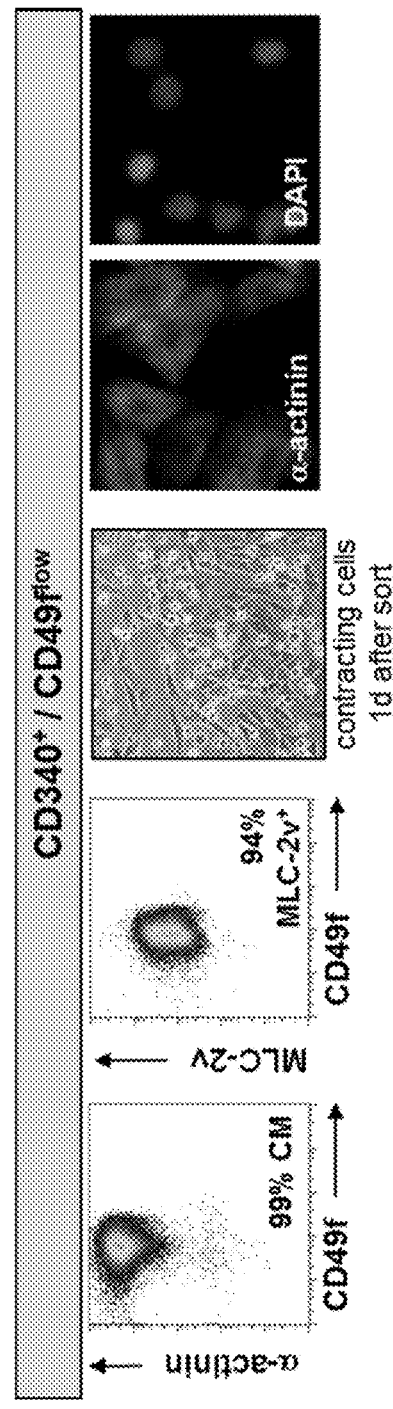
Figure 4F:
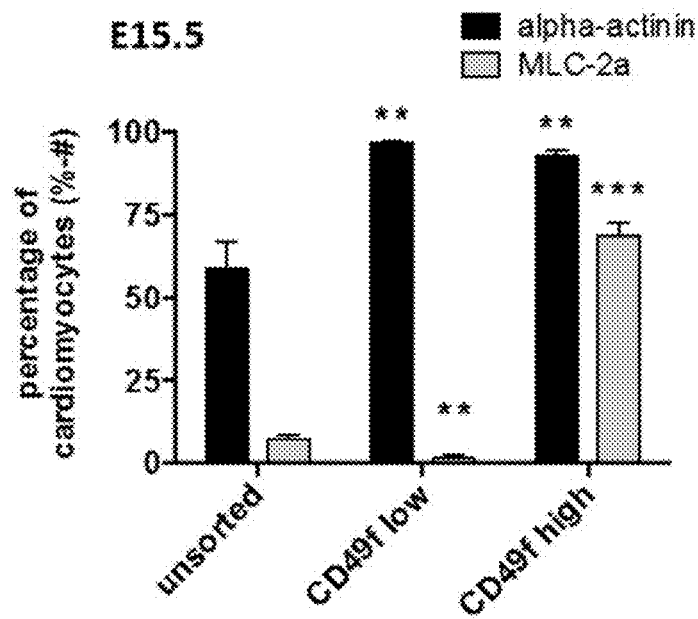
In FIGS. 4(F) and 4(G), fluorescence-activated cell sorting (FACS) of murine hearts according to Strategy 1 (E15.5) (FIG. 4(F)) and Strategy 2 (P2) (FIG. 4(G)) repeatedly resulted in an efficient purification of cardiomyocytes with significant enrichment of MLC-2a+ cells up to 70% in the CD49f$^{high}$ subpopulation.

In order to prove the separation strategies, fluorescence-activated cell sorting (FACS) was used to isolate cardiomyocyte subpopulations (FIG. 4(B)). Single cell suspensions of murine hearts (E15.5) were co-labeled with a PE-conjugated antibody against CD340 and a FITC-conjugated antibody against CD49f. Sorting gates were set on propidium iodide (PI) negative, CD340 positive, CD49f$^{low}$ cells (ventricular cardiomyocytes) as well as PI negative, CD340 positive, CD49f$^{high}$ cells (atrial cardiomyocytes). FIG. 4(C) shows marker analysis of the unsorted population. Flow cytometric re-analysis of the separated fractions revealed over 95% pure cardiomyocytes in both fractions (FIGS. 4(D) and 4(E)). Furthermore, it could be shown that the CD49f$^{high}$ subpopulation was specifically enriched for MLC-2a+ cells (from 9% of the complete heart up to 70%), whereas the CD49f$^{low}$ subpopulation was enriched for MLC-2v+ cells, i.e. ventricular cardiomyocytes (94%). These purification rates were reproduced in several independent experiments (FIG. 4(F), mean±SD, paired t test≤0.01, *≤0.01 vs. unsorted, n=4).

Figure 4G:
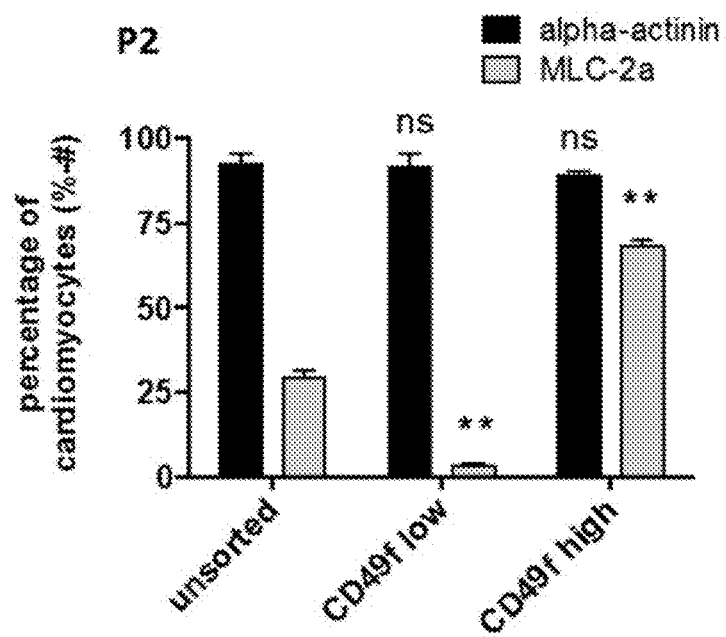

As shown in FIG. 4(G), similar purification rates could be observed when P2 hearts were pre-enriched for cardiomyocytes and then sorted for CD49f$^{high}$ and CD49f$^{low}$ cardiomyocyte subpopulations. This repeatedly resulted in a depletion of MLC-2a+ cells in the CD49f$^{low}$ subpopulation and an enrichment of MLC-2a in the CD49f$^{high}$ subpopulation of up to 70% (FIG. 4(F), mean±SD, paired t test**≤0.01 vs. unsorted, n=3).

The isolated cells were seeded on fibronectin-coated 48-well culture plates and were found to properly attach and to contract when analyzed 24 hours later. Immunofluorescence analysis confirmed sarcomeric structure of the cells and therefore purification of cardiomyocytes (FIGS. 4(D) and 4(E)).

In order to further characterize the nature of the sorted cell types, a minimum of 50,000 cells per fraction was collected directly after sorting and a gene expression analysis of the sorted cell fractions of four biological replicates was performed using one-color Agilent Whole Mouse Genome Oligo Microarrays. To identify differentially expressed genes, an ANOVA was performed (p<0.05) and statistical differences were determined by Tukey's test (p<0.05). Based on a 3.0 fold change cut-off, 663 out of 55,681 probes were found to be higher expressed in the E15.5 CD49f$^{high}$ cell fraction than in the E15.5 CD49f$^{low}$ cells, 256 probes were found to be lower expressed. Similar to that 931 probes were higher expressed in the P2 CD49f$^{high}$ fraction than in P2 CD49f$^{low}$ cells, 476 probes were lower expressed. The up- and down-regulated probes differed a little bit between the two developmental stages, 329 probes were up-regulated and 129 probes were down-regulated in both stages representing a set of marker genes for CD49f$^{low}$ and $^{high}$ cardiomyocytes. As expected we observed a higher expression of atrial marker genes (e.g. Myl7, Fgf12, Sln, Gja5, Nppa, Tbx5) in the CD49f$^{high}$ fraction whereas genes associated with a ventricular myocyte identity (e.g. Hey2, Irx4, Lbh, Myh7) were found in the down-regulated gene fraction. A list of selected markers is presented in FIGS. 4(H) and 4(I). Altogether, the results confirmed and strengthened our claim to specifically identify and isolate atrial cardiomyocytes by CD49f$^{high}$ expression and to purify ventricular cardiomyocytes by depletion of the CD49f$^{high}$ population from embryonic and postnatal hearts.

Example 4

Surface Marker-Based Detection of Pluripotent Stem Cell-Derived Cardiomyocytes

Next, flow cytometric analyses were performed in order to investigate the surface marker expression of murine embryonic stem cell (mESC)-derived cardiomyocytes (FIGS. 5(A), 5(B), 5(C), 5(D) and 5(E)). mESC were differentiated as embryoid body (EB) suspension culture for 10-16 days (with or without antibiotic selection). Single cell suspensions were co-labeled with antibodies against CD49f, CD61, CD340 or CD146 and antibodies against alpha-actinin or the atrial cardiomyocyte subtype muscle protein, MLC-2a. All mESC-derived alpha-actinin+ cells co-expressed CD49f, CD61, CD340 and CD146.

Figure 5E:
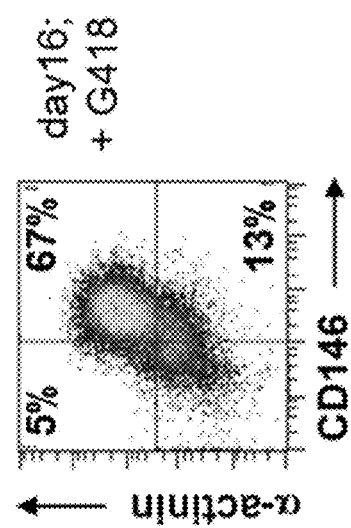
FIGS. 5(A) to 5(M) show data obtained from analysis of surface markers on pluripotent stem cell-derived cardiomyocytes. Cardiomyocytes derived from murine embryonic stem cells (mESC) expressed alpha-actinin with CD49f (FIG. 5(A)), and also expressed MLC-2a (FIG. 5(B)), CD61 (FIG. 5(C)), CD340 (FIG. 5(D)) and CD146 (FIG. 5(E)).
Figure 5D:
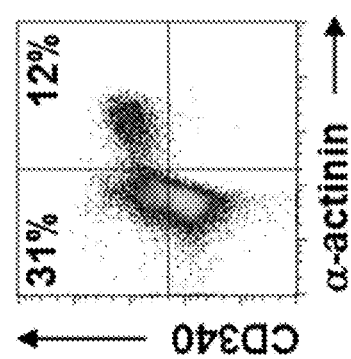
Figure 5B:
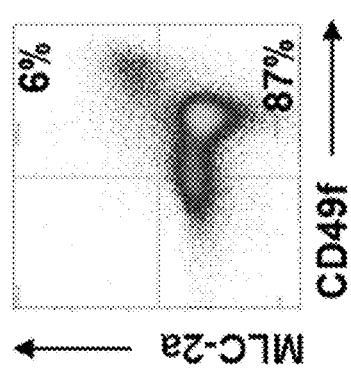
Figure 5C:
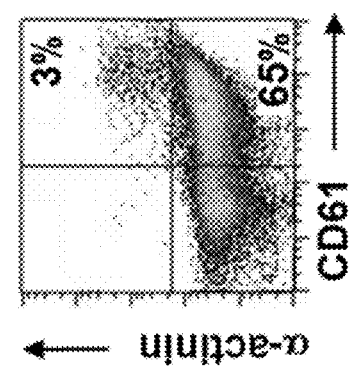
Figure 5A:
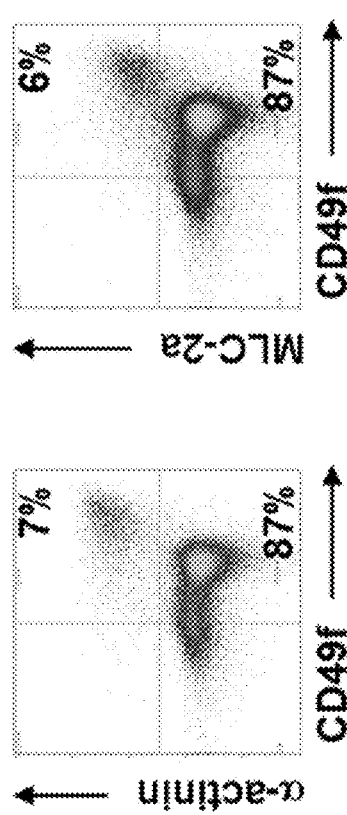
Figures 5F, 5G, 5H:
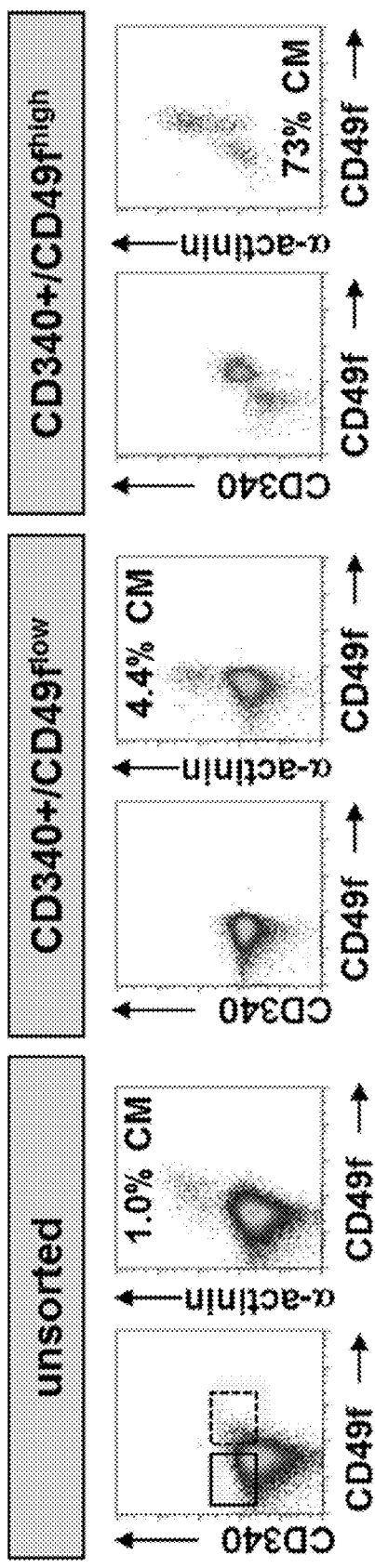
Figure 5I:
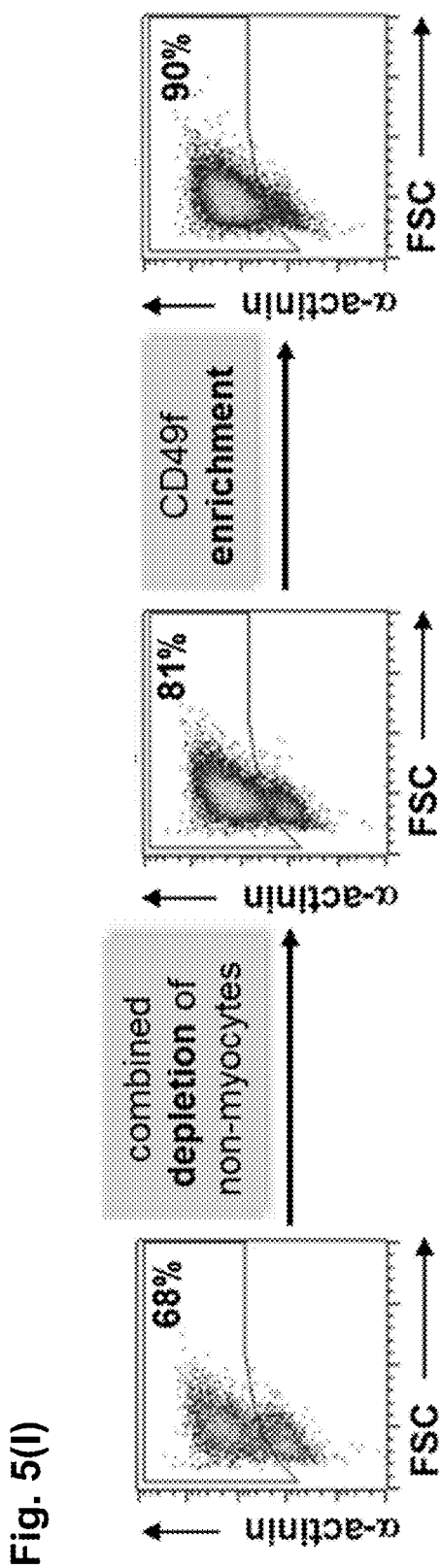
Figure 5J:
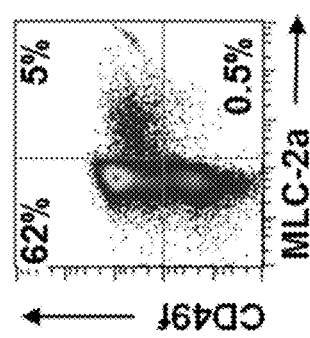
Figure 5K:
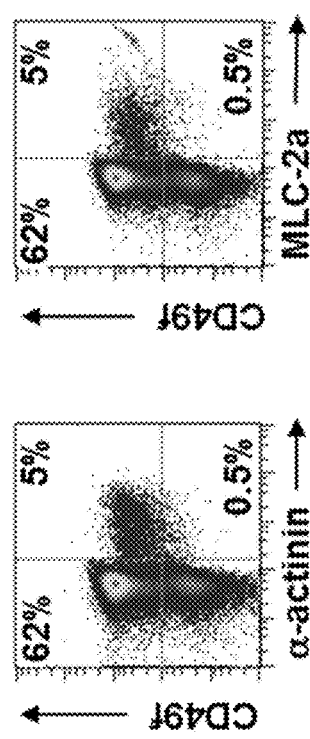
Figure 5M:
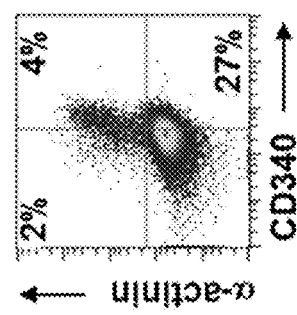
Figure 5L:
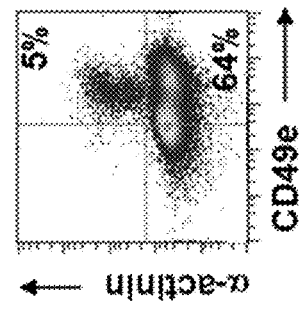

The in vitro generated cardiomyocytes were characterized by CD49f$^{high}$ expression (FIG. 5(A)). Furthermore, co-labeling with the antibody against MLC-2a showed the same pattern suggesting that the generated cardiomyocytes were all of an atrial cardiomyocyte phenotype (FIG. 5(B)). This also indicated that similar to murine cardiac tissue CD49f$^{high}$ expression could be used to specifically detect and isolate MLC-2a+ cells from differentiated murine stem cell cultures. Since CD49f was not exclusive for cardiomyocytes, we concluded that a second surface marker was required to successfully isolate mESC-derived cardiomyocytes. In a proof-of-principle experiment, FACS was used to isolate cardiomyocytes (FIGS. 5(F), 5(G), and 5(H)). CM7/1 cells were differentiated as EB suspension culture for 12 days. Single cell suspensions were co-labeled with a PE-conjugated antibody against CD340 and a FITC-conjugated antibody against CD49f. Sorting gates were set on propidium iodide (PI) negative, CD340 positive, CD49f$^{low}$ cells as well as PI negative, CD340 positive, CD49f$^{high}$ cells. Flow cytometric re-analysis of the fractions revealed an enrichment of cardiomyocytes from 1% to over 70% in the CD49f$^{high}$ population. For the CD49f$^{low}$ population we observed a slight increase in cardiomyocyte frequency (up to 4%). Next, we tested whether the sequential depletion of non-cardiomyocytes and enrichment of CD49f+ cells would increase the cardiomyocytes enrichment efficiency (FIG. 5(I)). CM7/1 cells were differentiated as EB suspension culture until day 11. Single cells were labeled with PE-conjugated antibodies against non-cardiomyocytes, i.e. CD15, CD326, CD105, followed by labeling with anti-PE MicroBeads®. Magnetic cell separation, i.e. removal of non-cardiomyocytes led to a rise of the CM content from 68 to 81%. The cells were then labeled with a biotin-coupled CD49f antibody followed by labeling with anti-biotin MicroBeads®. Magnetic separation reached a purification of mESC-derived cardiomyocytes from 68 to 90%.

Finally, flow cytometric analyses were performed in order to investigate the surface marker expression of human induced pluripotent stem cell (hiPSC)-derived cardiomyocytes (FIGS. 5(J), 5(K), 5(L) and 5(M)). Cells were cultured as monolayer until 90% confluency. Cardiac differentiation was induced by treatment with the GSK3 inhibitor CHIR99021 for 24 h and then with the Wnt inhibitor IWP4 between day 3 and day 5. Cells were cultured with medium changed every 2 to 3 days until day 22. Similar to atrial cardiomyocytes from mouse embryonic or neonatal heart as well as mouse embryonic stem cell-derived cardiomyocytes, all hiPSC-derived cardiomyocytes were MLC-2a+ cells and co-expressed CD49f, CD49e and CD340 (FIGS. 5(J), 5(K), 5(L) and 5(M)), suggesting, that cell-separation based on a combination of antibodies against CD340 and CD49f or CD49e will enable enrichment of MLC-2a positive cardiomyocytes derived from human pluripotent stem cells.

The invention claimed is:

1. A method for determining atrial and/or ventricular cardiomyocytes in a sample comprising cardiomyocytes, the method comprising the steps:
   a) contacting said sample:
      i) with an antigen-binding moiety specific for the CD49e antigen coupled to a fluorophore, and/or
      ii) with an antigen-binding moiety specific for the CD49f antigen coupled to a fluorophore,
   b) contacting said sample with an agent that is distinguishably distinct from the antigen binding moieties used in step (a), whereby the agent specifically labels cardiomyocytes in the sample,
   c) determining atrial and/or ventricular cardiomyocytes in the sample by detecting and comparing the intensity of labeling of cells in the sample for the CD49e antigen and/or the CD49f antigen with the intensity of labeling of the same cells by the agent, wherein
   ventricular cardiomyocytes are determined as being labeled with the agent and having more intense labeling of CD49e and/or less intense labeling of CD49f; and/or
   atrial cardiomyocytes are determined as being labeled with the agent and having more intense labeling of CD49f and/or less intense labeling of CD49e.

2. The method of claim 1, wherein said agent is an antigen-binding moiety specific for the cardiomyocyte cell surface marker CD340 coupled to a fluorophore.

3. A method of determining atrial cardiomyocytes according to claim 1, comprising the steps:
   a) contacting said sample with the antigen-binding moiety specific for the CD49f antigen coupled to a fluorophore,
   b) contacting said sample with the agent, thereby co-labeling the cardiomyocytes,
   c) determining atrial cardiomyocytes in the sample by detecting and comparing the intensity of labeling of cardiomyocytes in the sample for the CD49f antigen with the intensity of labeling of the same cells by the agent, wherein atrial cardiomyocytes are determined as having more intense labeling of CD49f.

4. A method isolating or purifying atrial cardiomyocytes in a sample comprising cardiomyocytes, the method comprising the steps:
   I) determining atrial cardiomyocytes in the sample according to the method of claim 3, and II) separating atrial cardiomyocytes determined in step (I) from other cells in the sample.

5. A method of determining ventricular cardiomyocytes according to claim 1, comprising the steps:
   a) contacting said sample with the antigen-binding moiety specific for the CD49f antigen coupled to a fluorophore,
   b) contacting said sample with the agent, thereby co-labeling the cardiomyocytes,
   c) determining ventricular cardiomyocytes in the sample by detecting and comparing the intensity of labeling of cardiomyocytes in the sample for the CD49f antigen with the intensity of labeling of the same cells by the agent, wherein ventricular cardiomyocytes are determined as having less intense labeling of CD49f.

6. A method isolating or purifying ventricular cardiomyocytes in a sample comprising cardiomyocytes, the method comprising the steps:
   I) determining ventricular cardiomyocytes in the sample according to the method of claim 5, and
   II) separating ventricular cardiomyocytes determined in step (I) from other cells in the sample.

7. A method of determining ventricular cardiomyocytes according to claim 1, comprising the steps:
   a) contacting said sample with the antigen-binding moiety specific for the CD49e antigen coupled to a fluorophore,
   b) contacting said sample with the agent, thereby co-labeling the cardiomyocytes,
   c) determining ventricular cardiomyocytes in the sample by detecting and comparing the intensity of labeling of cardiomyocytes in the sample for the CD49e antigen with the intensity of labeling of the same cells by the agent, wherein ventricular cardiomyocytes are determined as having more intense labeling of CD49e.

8. A method of determining atrial cardiomyocytes according to claim 1, comprising the steps:
   a) contacting said sample with the antigen-binding moiety specific for the CD49e antigen coupled to a fluorophore,
   b) contacting said sample with the agent, thereby co-labeling the cardiomyocytes,
   c) determining atrial cardiomyocytes in the sample by detecting and comparing the intensity of labeling of cardiomyocytes in the sample for the CD49e antigen with the intensity of labeling of the same cells by the agent, wherein atrial cardiomyocytes are determined as having less intense labeling of CD49e.

9. The method of claim 1, wherein the sample is contacted with both an antigen binding moiety specific for CD49e labeled with a first fluorophore, and a second antigen binding moiety specific for CD49f labeled with a second fluorophore that is different from the first fluorophore.

10. The method of claim 1, wherein the agent that specifically labels cardiomyocytes is an antigen binding moiety specific for CD61, CD146, CD112 or CD340.

11. A method isolating or purifying atrial and/or ventricular cardiomyocytes in a sample comprising cardiomyocytes, the method comprising the steps:
   I) determining atrial and/or ventricular cardiomyocytes in the sample according to the method of claim 1, and
   II) separating cardiomyocytes determined in step (I) from other cells in the sample.

12. A method for separating atrial cardiomyocytes and/or ventricular cardiomyocytes in a sample that is pre-enriched for cardiomyocytes, the method comprising the steps:
   a) contacting said pre-enriched sample with an antigen-binding moiety specific for the CD49e antigen coupled to a tag, and
   b) separating cardiomyocytes based on intensity of labeling of the cardiomyocytes by the tag;
   wherein atrial cardiomyocytes in the sample are less strongly tagged by the antigen binding moiety specific for CD49e antigen, and are thereby separated from ventricular cardiomyocytes which are more strongly tagged by the antigen binding moiety specific for the CD49e antigen.

13. The method of claim 12, wherein said sample has been pre-enriched for cardiomyocytes by a cell depleting method.

14. The method of claim 13, wherein said cell depleting method comprises the steps:
   I) contacting a non-enriched sample comprising non-cardiomyocytes and cardiomyocytes with combinations of antigen-binding moieties specific for cell surface markers of non-cardiomyocytes coupled to tags, thereby labeling the non-cardiomyocytes,
   II) isolating the non-labeled cardiomyocytes from said non-enriched sample.

15. The method of claim 14, wherein said cell surface markers of non-cardiomyocytes are selected from the group consisting of surface markers Sca-1, CD15, CD31, CD38, CD45, CD49b, CD49d, CD54, CD66a, CD73, CD90.1, CD90.2, CD105, CD117, CD138, CD140a, CD140b, CD184, CD326, with the proviso that for PSC-derived non-cardiomyocytes at least one cell surface marker is CD31, CD66a, CD38, CD49b, Sca-1, or CD105 and at least one cell surface marker is CD326 or CD15, or with the proviso that for neonatal non-cardiomyocytes at least one cell surface marker is CD31, CD105, or CD146 and at the other cell surface markers are CD45, CD51 and CD90.2.

16. The method of claim 14, wherein in said cell depletion method said tag is a magnetic particle, and wherein said isolation of said non-labeled cardiomyocytes of said non-enriched sample is performed by magnetic cell sorting.

17. The method of claim 12, wherein in said method comprises separation of cells by flow cytometry.

18. The method of claim 12, wherein said antigen binding moiety is an antibody or fragment thereof.

19. The method of claim 12, wherein said atrial and/or ventricular cardiomyocytes are human or murine cells.

20. A method for separating atrial cardiomyocytes and/or ventricular cardiomyocytes in a sample that is pre-enriched for cardiomyocytes, the method comprising the steps:
   a) contacting said pre-enriched sample with an antigen-binding moiety specific for the CD49f antigen coupled to a tag, and
   b) separating cardiomyocytes based on intensity of labeling of the cardiomyocytes by the tag;
   wherein atrial cardiomyocytes in the sample are more strongly tagged by the antigen binding moiety specific for CD49f antigen, and are thereby separated from ventricular cardiomyocytes which are less strongly tagged by the antigen binding moiety specific for the CD49f antigen.

21. A method for determining atrial and/or ventricular cardiomyocytes in a sample that is pre-enriched for cardiomyocytes, the method comprising the steps:
   a) contacting said sample with an antigen-binding moiety specific for the CD49e antigen coupled to a fluorophore,
   b) contacting said sample with an antigen-binding moiety specific for the CD49f antigen coupled to a fluorophore, c) determining atrial and/or ventricular cardiomyocytes in the sample by detecting binding of the antigen-binding moiety to the CD49e antigen expressed in the cells in a) and detecting binding of the antigen-binding moiety to the CD49f antigen expressed in the cells in b) and comparing the intensity of labeling of cells in the sample for the CD49e antigen with the intensity of labeling of the same cells for the CD49f antigen, wherein ventricular cardiomyocytes are determined as having more intense labeling of CD49e as compared with CD49f; and/or atrial cardiomyocytes are determined as having more intense labeling of CD49f as compared with CD49e.

22. The method of claim 21, further comprising contacting said sample with an antigen-binding moiety specific for the cardiomyocyte cell surface marker CD340 coupled to a fluorophore.

* * * * *